(12) United States Patent
Kamal et al.

(10) Patent No.: US 12,042,633 B2
(45) Date of Patent: Jul. 23, 2024

(54) SYRINGE

(71) Applicant: Revive Innovations +Ltd, London (GB)

(72) Inventors: Abhisheik Kamal, London (GB); Urshita Gautam, London (GB); Alexander Kalogroulis, Surrey (GB)

(73) Assignee: REVIVE INNOVATIONS + LTD., London (GB)

( * ) Notice: Subject to any disclaimer, the term of this patent is extended or adjusted under 35 U.S.C. 154(b) by 0 days.

(21) Appl. No.: 17/622,410

(22) PCT Filed: Jun. 23, 2020

(86) PCT No.: PCT/GB2020/051518
§ 371 (c)(1),
(2) Date: Dec. 23, 2021

(87) PCT Pub. No.: WO2020/260867
PCT Pub. Date: Dec. 30, 2020

(65) Prior Publication Data
US 2022/0355031 A1 Nov. 10, 2022

(30) Foreign Application Priority Data
Jun. 23, 2019 (GB) .................................. 1908957

(51) Int. Cl.
*A61M 5/19* (2006.01)
*A61M 5/178* (2006.01)
(Continued)

(52) U.S. Cl.
CPC .............. *A61M 5/19* (2013.01); *A61M 5/178* (2013.01); *A61M 5/20* (2013.01);
(Continued)

(58) Field of Classification Search
CPC ................... A61M 5/19; A61M 5/281; A61M 2005/3267; A61M 2005/2013;
(Continued)

(56) References Cited

U.S. PATENT DOCUMENTS

| 748,424 | A | * | 12/1903 | Schmidt | ............... | A61M 5/283 |
| | | | | | | 604/231 |
| 2,567,001 | A | * | 9/1951 | Watson | ................. | A61M 5/284 |
| | | | | | | 604/88 |

(Continued)

FOREIGN PATENT DOCUMENTS

| CN | 1030529 A | 1/1989 |
| EP | 1980283 A1 | 10/2007 |

(Continued)

OTHER PUBLICATIONS

Search Report issued in related application numbered GB2009583.2 on Aug. 20, 2020.

(Continued)

*Primary Examiner* — James D Ponton
*Assistant Examiner* — Hong-Van N Trinh
(74) *Attorney, Agent, or Firm* — Brian J. Colandreo; Jeffrey T. Placker; Holland & Knight LLP

(57) ABSTRACT

A syringe (200, 400) for use in a medication delivery device (100) comprises a vial. The vial (201, 411) comprises a chamber (206). The chamber is configured to receive a piston or plunger (205, 416). The syringe further comprises a needle attachment point (202), for the attachment of a hypodermic needle (204). The chamber is offset from the needle attachment point.

19 Claims, 36 Drawing Sheets

(51) Int. Cl.
*A61M 5/20* (2006.01)
*A61M 5/28* (2006.01)
*A61M 5/34* (2006.01)

(52) U.S. Cl.
CPC ....... *A61M 2005/206* (2013.01); *A61M 5/281* (2013.01); *A61M 2005/342* (2013.01)

(58) Field of Classification Search
CPC ...... A61M 2005/206; A61M 2005/342; A61M 5/2422; A61M 5/2425; A61M 5/282; A61M 5/2429–2005/247; A61M 5/283–2005/287; A61J 1/2089
See application file for complete search history.

(56) References Cited

U.S. PATENT DOCUMENTS

| | | | |
|---|---|---|---|
| 3,841,329 A | 10/1974 | Killinger | |
| 4,738,660 A | 4/1988 | Lucas | |
| 4,936,830 A | 6/1990 | Verlier | |
| 5,542,934 A | 8/1996 | Silver | |
| 6,547,101 B1* | 4/2003 | Sogaro | A61M 5/19 222/137 |
| 2008/0167621 A1* | 7/2008 | Wagner | A61M 5/19 600/432 |
| 2008/0188807 A1* | 8/2008 | Caizza | A61M 5/508 604/110 |
| 2009/0240232 A1* | 9/2009 | Gonnelli | A61M 5/1407 604/141 |
| 2010/0137830 A1* | 6/2010 | Glejbol | A61M 5/31596 604/153 |
| 2013/0046239 A1* | 2/2013 | Gonnelli | G01F 11/022 604/150 |
| 2019/0151549 A1* | 5/2019 | Young | A61M 5/2033 |

FOREIGN PATENT DOCUMENTS

| | | |
|---|---|---|
| GB | 2 206 800 A | 7/1988 |
| GB | 2 418 616 A | 4/2006 |
| GB | 2 477 046 A | 7/2011 |
| JP | 2006-158980 A | 6/2006 |
| JP | 2009-531143 A | 9/2009 |
| WO | 2018229117 A1 | 12/2018 |
| WO | 2020/260867 A1 | 12/2020 |

OTHER PUBLICATIONS

Search Report issued in related application numbered GB1908957.2 on Dec. 12, 2019.
International Search Report and Written Opinion issued on Sep. 18, 2020 in counterpart International Application Serial No. PCT/GB2020/051518.
Chinese First Office Action issued in Application Serial No. 202080059673.8 on Dec. 21, 2022.
Office Action cited in related Japanese Application Serial No. 2022-523732 dated Feb. 6, 2024.

\* cited by examiner

SYRINGE

CROSS-REFERENCE TO RELATED APPLICATIONS

This application is a U.S. National Stage of International Patent Application No. PCT/GB2020/051518, filed 23 Jun. 2020, which claims priority to Great Britain Patent Application No: 1908957.2, filed on 23 Jun. 2019. The disclosures of which are incorporated herein by reference in their entirety.

FIELD OF THE INVENTION

The present invention relates to the field of syringes, and particularly, but not exclusively, syringes for use in a medication delivery devices, and medication delivery devices.

BACKGROUND TO THE INVENTION

Some medical conditions require rapid response through the administration of medication. This response will often be required before a patient can be brought to a medical professional. As such self-administered auto-injectors are available that allow a patient or another person to administer the medication. For example, auto-injectors may be used in the treatment of anaphylactic shock, in which case epinephrine may be the medication. Such devices may also be used in the treatment of other medical conditions to administer different medications.

Medication delivery devices known in the art are conventionally linearly constructed. Their construction may be summarised as a needle followed by a cylindrical vial holding the medication and a plunger to decrease the volume and increase the pressure in the vial, thereby forcing the medication out through the needle.

It is an aim of the present invention to provide an improved medication delivery device over those known in the art.

SUMMARY OF THE INVENTION

According to an aspect of the invention there is provided a syringe e.g. for use in a medication delivery device. The syringe may comprise one or more vials. The or each vial may comprise a chamber. The chamber may be formed as a bore in a cylinder, the cylinder being comprised within the vial. The chamber may be configured to contain a fluid. The vial may be configured to receive a piston. The syringe may comprise the piston. The syringe may further comprise a needle attachment point, for the attachment of a hypodermic needle. The chamber may be offset e.g. laterally within the syringe from the needle attachment point. The needle may be integral with the syringe or may be attachable thereto (and detachable therefrom).

Reference to the chamber being "offset" from the needle attachment point is intended to cover configurations where e.g. at least a part or all of the chamber is offset from the needle attachment point and/or wherein at least a part or all of the chamber is fluidly connected to the needle attachment point by one or more fluid channels or connectors. By "offset" it may be meant that a part or all of the chamber is laterally offset. Laterally refers to a dimension that is transverse to an injection direction, wherein the injection direction corresponds to the axis of a needle when fitted to the syringe.

According to another aspect or embodiment of the invention there is provided a syringe e.g. for use in a medication delivery device and e.g. may be the syringe of the above aspect. The syringe may comprise a vial. The vial may comprise a plurality of interconnected chambers. The vial may be configured to receive a piston. The syringe may comprise the piston.

Where there is a plurality of or multiple chambers, they may be fluidly connected to each other and/or to the needle attachment point via one or more fluid channels or pathways. The fluid pathway(s) may have a small or narrow cross section in the longitudinal direction and may have at least one smaller dimension than the chambers. Preferably the chambers are substantially the same volume capacity.

For either aspect, advantageously, the syringe has a different configuration to a standard syringe, and may have uses where a conventional syringe is not appropriate or desirable e.g. due to its size or appearance. In conventional syringes the chamber is in series with the needle attachment point. As the invention provides for the chamber being offset with i.e. not in series with the needle attachment point, different configurations of syringe are possible e.g. wider and/or flatter and/or shorter compared with a standard elongate syringe.

Either of the above aspects may be limited or characterised by the below embodiments:

The chamber may be a single chamber or may be or may comprise a pair of chambers or multiple chambers. The or each chamber may be configured to receive a piston, otherwise known as a plunger. Where there is a plurality of chambers, two or more of the chambers may be symmetrically arranged about the needle attachment point. In other words the needle attachment point and chambers may be provided in parallel. The needle attachment point and chambers may be provided at least partly in parallel. The needle attachment point and chambers may be provided at least partially aligned or at least partially overlapping in the lateral direction. The needle attachment point and chambers may be provided not in series. This provides for spaced utilisation compared to arranging a chamber and needle attachment point in series. The symmetrical arrangement provides a symmetric and even distribution of force during the administration of medication from the device. Such a configuration could be more appropriate if the application demands so. The chambers may be of substantially rectangular cross section. Substantially rectangular may be considered to include shapes having similarities to rectangles, including rounded rectangles, discorectangles, rounded trapezoids etc. A main criteria may be that one dimension of the cross section is greater than another dimension of the cross section. The chambers may instead comprise bores formed within cylinders of the vial. The chamber may therefore be of substantially circular cross section. The chamber may be formed from a plurality of connected chambers. A pressure relief hole may be provided between two or more of the connected chambers. The pressure relief hole may reduce pressure build up in one or more parts of the chambers than if a pressure relief hole is not used.

In embodiments of the invention, the syringe may be configured to provide a plunging action in a direction counter to a medication delivery direction. The syringe may be configured to provide a plunging action in a direction going from proximal to distal, as opposed to the medication delivery direction which is distal to proximal. This further reduces the space required, allowing for a more compact syringe. Such an arrangement may also be configured to allow the plunger or plungers to serve a secondary function of acting as a shock absorber and thereby reducing impact force on the vial or its chambers.

Embodiments of the invention may comprise a pair of pistons. Where a pair of chambers is provided, one piston may be provided to be received in each chamber.

In other embodiments, a single chamber or multiple chambers may be provided and/or a single or multiple pistons may be correspondingly provided.

Embodiments of the invention may comprise attachment means, wherein the attachment means is configured to receive and/or cooperate with a reciprocal or mutually cooperating attachment means of a syringe carrier. The attachment means of the syringe may be or comprise a female attachment means. The attachment means of the syringe may be or comprise a slot, groove, channel, hole, bore, bearing or other aperture. The attachment means of the syringe may be formed in a wall, body or surface of the vial or syringe. The attachment means of the syringe may be formed so as to interlock with a reciprocal or mutually cooperating attachment means of a syringe carrier. In some embodiments the attachments means of the syringe carrier and the syringe are slidably connectable such that the syringe may translate linearly with respect to the syringe carrier attachment means.

According to a further aspect of the invention there is provided a medication delivery device comprising a syringe of any of the preceding aspects or embodiments.

Embodiments of the invention may comprise a housing, optionally having a distal end and a proximal end. The housing may be a single component or may be formed of a plurality of housing parts. Embodiments of the invention may comprise a cover. The cover may be removably attachable to the housing. Embodiments of the invention may comprise an energy storage means, optionally provided within the distal end of the housing. Embodiments of the invention may comprise an actuator assembly optionally having a distal end and a proximal end. The distal end may be provided within the housing and the proximal end may extend beyond the housing. The actuator assembly may comprise a plurality of actuators, actuating components and/or actuation subsystems. In an embodiment, there is provided a proximal actuator part and a distal actuator part. In some embodiments the distal actuator part may be referred to as a chassis and the proximal actuator part may be referred to simply as an actuator, or vice-versa. The syringe may be attached or attachable to the energy storage means. The actuator assembly (e.g. a proximal actuator part) may be configured to actuate the energy storage means to move the syringe towards the proximal end and expose the needle for use. A distal actuator part may be configured to move the device components relative to each other to cover the needle after use. Alternatively a single actuator assembly may be provided and configured for both functions.

Embodiments of the invention may provide for the syringe to be movable through a penetration stage and an injection stage.

The penetration stage is a stage in which the needle is configured to penetrate the skin of a patient. The injection stage is a stage in which the syringe is configured to deliver a medicament to the user. The injection stage follows the penetration stage. The injection stage may comprise movement through a final 15 mm or less. The injection stage may comprise movement through a final 1 mm or more. Preferably the injection stage comprises movement through 7 mm or less. Preferably the injection stage comprises movement through 3 mm or more. Still preferably the injection stage comprises movement through approximately 5 mm. The syringe may be configured only to deliver medicament during the injection stage. This may ensure that the needle is at a suitable depth below an upper skin surface of the patient for administering the medicament. The suitable depth could be subcutaneous or intramuscular depending on the application.

The syringe may be movable through the penetration stage and/or injection stage via the application of a force derived from the energy storage means.

Embodiments of the invention may comprise a stop wall. The stop wall may be formed in the housing. The stop wall may be configured to cooperate with the piston to transition from the penetration stage to the injection stage. The stop wall may be considered to be a 'plunger pusher' in that it interacts with the plunger/piston to push it into the chamber of the syringe in order to push the medicament out through the needle. Rather than a wall of the housing the stop wall may be formed as a projection. The wall or projection may be provided on other components than the housing. For example the wall or projection could be provided on any part that moves relative to the syringe when in use. Such a component may be a distal actuator part or a chassis.

Embodiments of the invention may comprise a syringe carrier. The syringe carrier may comprise an attachment means configured to receive and/or cooperate with a reciprocal attachment means of the vial or syringe. The attachment means of the syringe carrier may be or comprise a male attachment means and, optionally, the male attachment means may be or comprise a protrusion.

Alternatively, the attachment means of the vial may be or comprise a male attachment means and the attachment means of the syringe carrier may be or comprise a female attachment means. The features and/or characteristics of the male/female attachment means are interchangeable between the syringe carrier and the vial. Embodiments are envisaged where one is receivable and optionally interlockable within the other.

In other embodiments of the invention the syringe carrier and syringe are slidably connected. The syringe carrier may comprise an attachment means in the form of a guide rail. The guide rail may provide a locating means for the syringe. The guide rail may provide a means to control a translation of the syringe from the distal end of the device towards the proximal end of the device.

Embodiments of the invention may comprise a passage for a needle. The passage for the needle may be formed in the proximal end of the actuation assembly.

In embodiments of the invention the actuation assembly may be actuated via application of a force at the proximal end of the actuation assembly. Optionally, this occurs via a manually applied force.

In embodiments of the invention the actuation assembly may be configured to extend to cover the needle after an injection is performed.

Embodiments of the invention may comprise a distal actuator part and a proximal actuator part. The distal actuator part and the proximal actuator part may form the actuator assembly.

The medication delivery device may be further configured to translate the proximal actuator part away from the distal actuator part to cover the needle after an injection is performed. Covering the needle after an injection is performed may therefore comprise translating the proximal actuator part away from the distal actuator part.

The actuator assembly may comprise one or more actuator springs. The actuator spring may be configured to provide a force to translate the proximal actuator part away from the distal actuator part. The spring may be a helical spring. The spring may be a compression spring. In other embodiments, the spring may be an expansion spring. The proximal and distal actuator parts may be biased toward or away from each other using different kinds of springs (compression, expansion etc.) and may be held in an initial/primed position through the provision of cooperating features on the housing and/or cover and/or the proximal and distal actuator parts etc.

The distal actuator part and the proximal actuator part may comprise one or more corresponding detents. The detents may be configured to disengage upon actuation of the device. The detents may also be described as tabs, stop faces, or tabs comprising stop faces.

According to a yet further aspect of the invention there is provided a medication delivery device comprising a chamber for storing medication. The medication delivery device may comprise a needle attachment point for receiving a hypodermic needle. The medication delivery device may comprise an energy storage means. The medication delivery device may comprise an actuator, for releasing the energy stored in the energy storage means. The needle attachment point may be offset from the chamber.

According to yet another aspect of the invention there is provided a method of using the device according to one or more of the preceding aspects and optionally according to the embodiments provided. The method may comprise actuating a or the energy storage means to move the syringe towards the proximal end of the device.

According to yet another aspect of the invention there is provided a method of manufacturing the device according to one or more of the preceding aspects and optionally according to the embodiments provided. The method may comprise providing a chamber that is offset from the needle attachment point.

In an embodiment for any above aspect, the housing may surround all or part of the syringe and/or other components. The housing may have an open or a substantially open end from which the needle can project during use of the device. A cover may be provided that is configured to attach and/or be receivable on, around, in, or over the open end of the housing. The cover may be configured to provide protection so the needle cannot inadvertently be triggered or injure anyone. The housing and/or cover may be configured to be securable to each other via one or more corresponding and/or cooperating features such as detents, male/female elements (such as projections, slots, hooks, apertures, cantilevers, stops etc.).

One or more indicia may be provided on any part of the syringe/device e.g. on the cover and/or housing. The indicia may be textual and/or visual and/or textured and may convey warnings or instructions for use.

For any above aspect or embodiment, advantageously, the syringe/medication delivery device has a different physical/geometrical configuration to a standard syringe. In conventional syringes the chamber is in series with the needle attachment point. As the invention provides for the chamber being offset with i.e. not in series with the needle attachment point, different configurations of syringe are possible e.g. wider and/or flatter and/or shorter compared with a standard elongate syringe. This means the device is more easily stowable and transportable.

The syringe/device can, advantageously, be used for self-administering medication or administering medication to another individual.

One or more retaining and/or cooperating members may be provided on one or more of the interior of the housing, the cover and/or on the syringe carrier and/or on the actuator assembly and/or on the vial so as to cooperate with or engage with corresponding other features on one or more of said component parts to retain the syringe or the device in one or more predetermined positions. For example, the device may be secured in a primed position, ready for use. Alternatively, the device may be secured in a non-primed position e.g. when no medication is inside or after it has been used.

The piston(s) may comprise a hard and/or rigid portion and/or a soft and/or pliable or deformable portion. The softer part may provide a sealing means between the piston and the syringe. The pistons may also be referred to as plungers and may comprise sealing ridges that interface with the syringe to provide a sealing means.

The optional features from any aspect may be combined with the features of any other aspect, in any combination.

Features which are described in the context of separate aspects and embodiments of the invention may be used together and/or be interchangeable wherever possible. Similarly, where features are, for brevity, described in the context of a single embodiment, those features may also be provided separately or in any suitable sub-combination. Features described in connection with the method may have corresponding features definable with respect to the device and use of the device, and these embodiments are specifically envisaged.

BRIEF DESCRIPTION OF THE DRAWINGS

Embodiments of the invention will now be described, by way of example only, with reference to the accompanying drawings, in which.

DESCRIPTION

Figure 1:
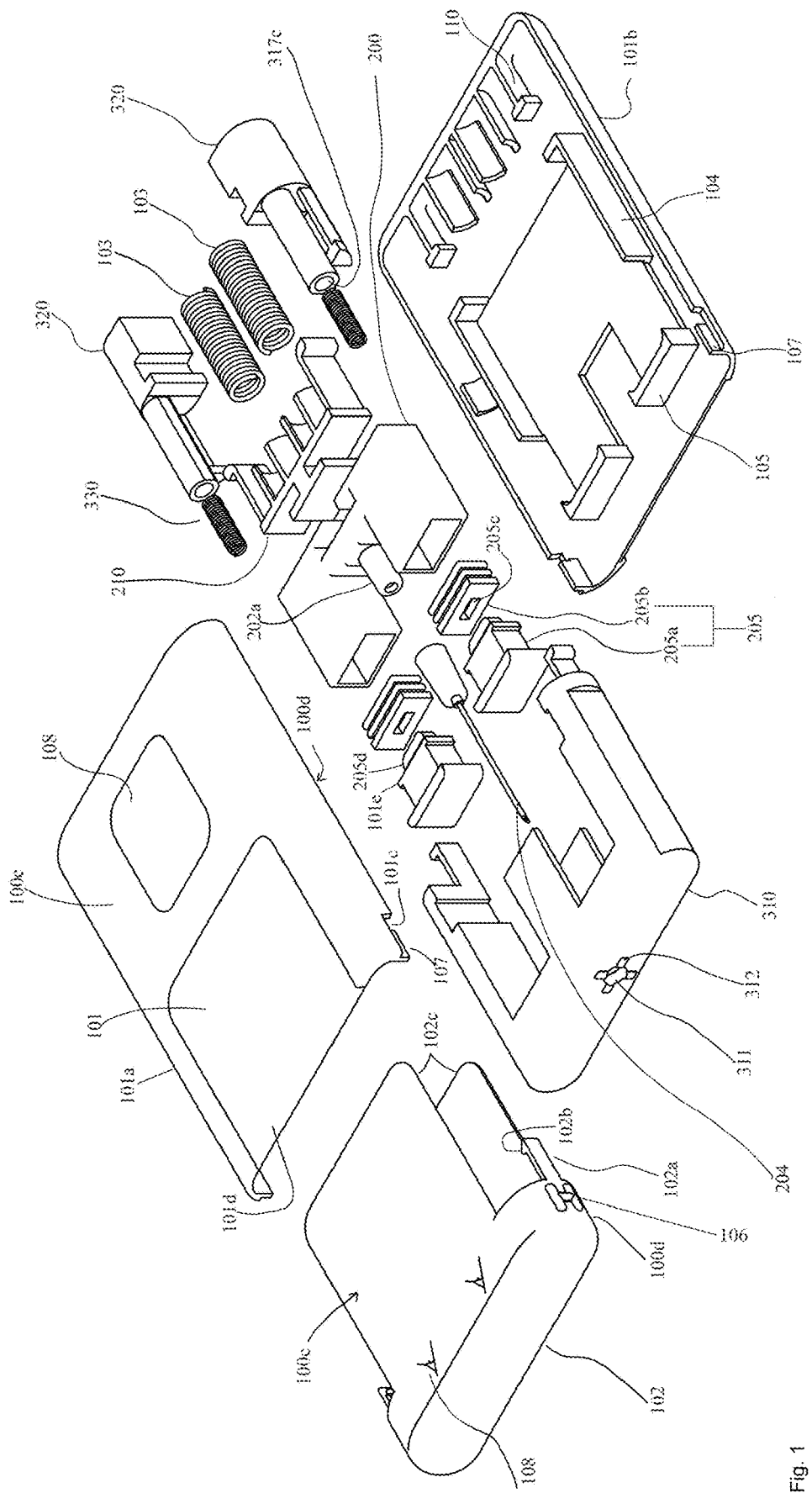
FIG. 1 shows an exploded view of a medication delivery device.

A medication delivery device 100 and some of its core components are described below with reference to the figures. The device itself is designed to be easily stowable and transportable. For this reason it has a substantially flat form and small size compared to medication delivery devices known in the art. By flat, it is meant that the thickness of the device is substantially smaller than its width and length. The length and width of the device is comparable to that of a credit card, thereby making it suitable for storing in a pocket for example. The device 100 is between substantially 84 and 98 mm long, substantially 52 and 68 mm wide and between substantially 11.5 mm and 15.5 mm thick. More specifically the device 100 is between 87 and 94 mm long by between 55 and 58 mm wide and between 11.5 mm and 13.5 mm thick. For example the device 100 may be substantially 87 mm long, substantially 55 mm wide and substantially 11.5 mm thick and configured to deliver a 0.5 ml dose. It will be appreciated these are given as examples only. Dimensions can be varied depending on the practical requirements of the application such as dose size, volume of liquid to be carried, etc.

The device 100 and its components are described as follows: reference to "proximal" is to components at or towards a patient on which the device 100 is to be used. Reference to "distal" is to components at an opposite end of the device or away from a patient on which the device 100 is to be used. The proximal end 100a of the device 100 refers to the end of the device enclosed by a cover 102 and is the end which is brought into contact with a target area of a body of a patient. The distal end 100b of the device 100 refers to the end of the device opposite the proximal end of the device 100. An axis (not shown) extending linearly between the distal and proximal ends is described as being longitudinal. The device has two large or major surfaces 100c, 100d. Functionally the major surfaces (which may be considered as a front and back of the device 100) are interchangeable. The sides of the device 100 extend between the proximal and distal ends 100a, 100b and the two major surfaces 100d, 100d. The axis extending linearly between the sides is described as being lateral.

The device 100 is configured to be either self-administered or administered by another individual. As such this specification refers to users and patients, wherein the user is the administrant and the patient is the recipient. As the device 100 may be self-administered the user and patient may be one and the same.

FIG. 1 is an exploded view of the medication delivery device 100. The medication delivery device 100 has multiple interconnectable or interconnected parts. An outer periphery of the medication delivery device 101 is defined by a housing 101 and a cover 102. The housing 101 contains a plurality of internal components which will be discussed below. The cover 102 is removably connectable to the housing 101 (or vice versa) in order to enclose a proximal end of the housing 101. Alternatively the cover 102 could simply attach to the end of the housing 101 without substantially enclosing the proximal end of the housing 101.

The housing 101 comprises a first e.g. a front part 101a and a second e.g. a back part 101b. The first part 101a and the second part 101b are configured to be connectable together to enclose inner components. In an embodiment, the housing is instead of a single or unitary construction. In an embodiment, the cover 102 and the housing 101 are formed from a rigid material. For example, they may be formed of a plastics material. The plastic may be PP (polypropylene) or ABS (Acrylonitrile Butadiene Styrene). The plastic parts may be formed using injection moulding or other known, suitable processes. Alternatively, the cover 102 and the housing 101 could be formed (e.g. cast and machined) from a metal such as aluminium. One or more cover detents 102a are provided on the cover 102 which correspond to and/or are receivable in one or more recesses 101c on the housing 101. The detent 102a has a catch 102b (e.g. a hook) configured to engage with a detent 107 provided in or near the recess 101c on the housing 101. The engagement of the detents 102a, 107 enables the cover to be retained on the housing 101 e.g. during transport and storage. To remove the cover 102, one or more detent 106 on the lateral/side faces of the cover 102 can be gripped and pulled longitudinally away from the housing 101. The pressure from the motion pushes the catch outwards to disengage the cover detents 102a from the housing detents 107. Additional similarly corresponding detents and housing recesses (not shown) could be provided on the major surfaces 100c, 100d. Such an embodiment would result more force required to remove the safety cover 101 and may be preferable for specific contexts. Alternatively or additionally, one or more other attachment or securing means may be provided to secure the cover 102 to the housing. One or more male/female attachment members may be provided on the cover 102/housing 101 (or vice versa), and/or one or more mutually cooperating attachment members (e.g. interengageable hooks) may be provided on the cover 102/housing 101 (or vice versa).

In the embodiment shown the cover 102 has short lateral sides and longer major (front/back) surfaces 102c. As such, apart from the detents 102a, the cover has partially open lateral sides. In other embodiments the lateral sides are closed or substantially closed. In either case, the two major surfaces 102c of the cover are therefore provided in the form of plates projecting away from the proximal end of the cover 102. In the embodiment shown, the major surfaces 100c, 100d of the housing 101 comprise a recessed or inset portion 101d configured to receive the plates 102c. Preferably, when the plates 102c are located in the recess 101d the exteriors of the cover 102 and the housing 101 are substantially flush with respect to each other. In other embodiments, the cover 102 may e.g. attach on to the proximal end of the housing e.g. clip on.

One or more indicia 108 in the form of graphics and/or visual and/or textual instructions may be provided on one or more of the outer surfaces of the housing 101 and/or the cover 102. One or more of these indicia 108 may be formed as part of the manufacturing process and therefore be formed as raised or sunken profiles in surfaces of the device 100. Other indicia 108 may be provided by printing directly on to the surface of the device. Other indicia 108 may be provided as adhesive stickers. Removing the cover 102 may reveal additional indicia 108 on the housing 101 e.g. on or in the recessed or inset portion 101d. Such additional indicia 108 on the housing 101, revealed by the removal of the cover 102, may display warnings and/or instructions. The warning and instructions may state, amongst other things, that the device is in a 'ready' state and that care should be taken to prevent accidental injection. The cover 102 may feature indicia 108 indicating a direction to pull the cover in order to remove. These indicia 108 may be in the form of arrows indicating the correct direction. The word "PULL" or similar may also be used.

The housing 101 or, in embodiments, one or more of the front part 101a and back part 101b of the housing 101, comprise one or more ribs and/or protrusions 104 configured to retain the internal components of the device 100. One or more of the ribs and/or protrusions 104 may also be configured to provide structural rigidity to the device 100. The ribs and/or protrusions 104 can therefore aid the housing 101 to resist crushing or breaking when the device 100 is in transport (e.g. in a pocket or bag) or when used. Instead of one or more ribs and/or protrusions, other retaining means could be provided e.g. a wall, stop, ridge, detent etc.

The internal components comprise a syringe carrier assembly and an actuator assembly, both of which are shown disassembled in FIG. 1 into their constituent parts and are described in more detail below, and an energy storage means 103. The energy storage means 103 preferably comprises a spring, e.g. a helical spring. In the embodiment shown, a pair of parallel helical springs 103 is provided. It will be appreciated that one or more other springs, and/or different types of springs, and/or one or more other biasing means may additionally or instead be used.

Figure 2:
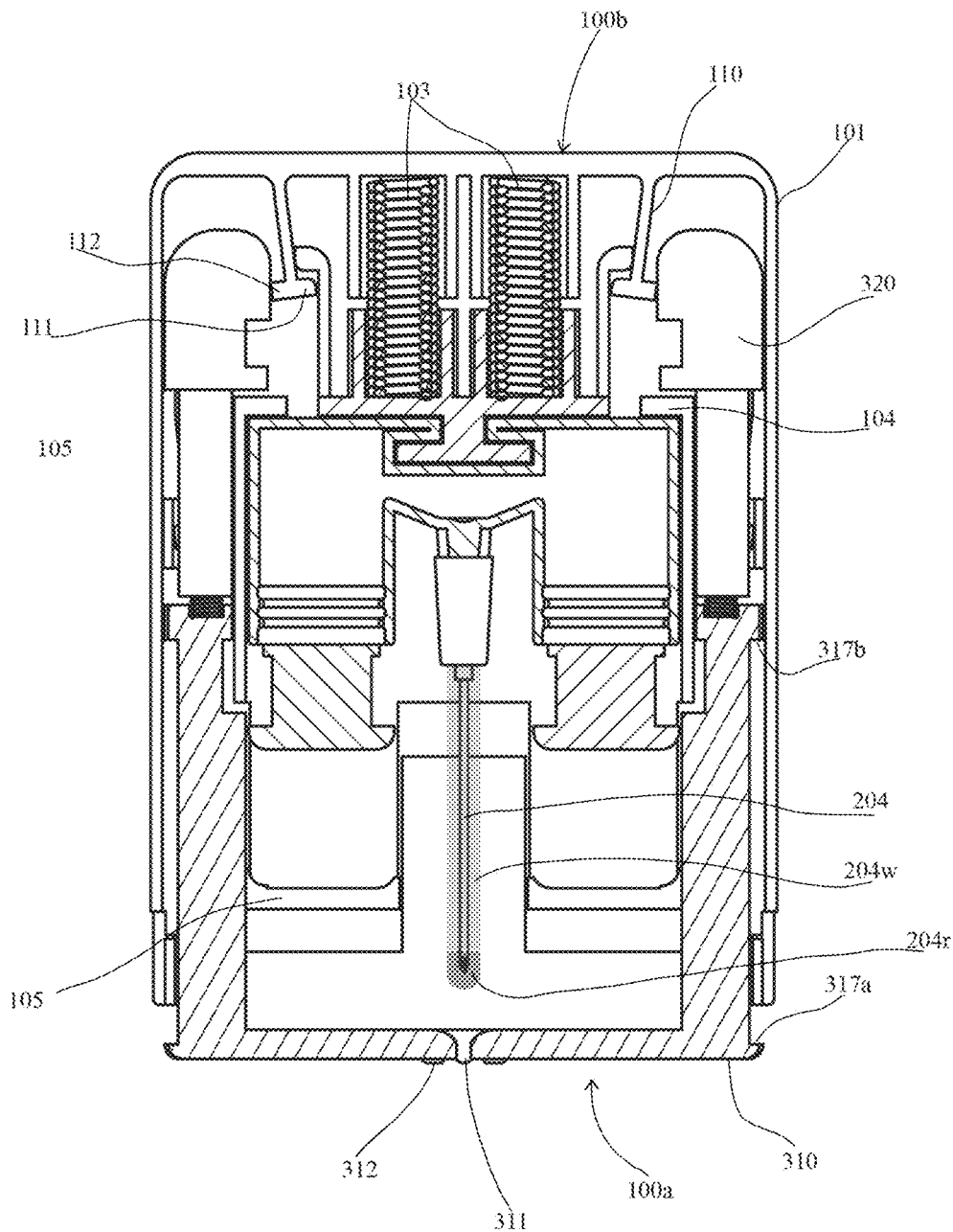
FIGS. 2 and 2a show longitudinal and transverse cross sectional views of the medication delivery device of FIG. 1 when assembled.

FIG. 2 shows a cross section of the medication delivery device 100 when assembled but without the cover 102. In the configuration shown, the device 100 has had the cover 102 removed and is primed for use. A proximal actuator part 310 of the actuator assembly protrudes beyond the proximal end of the housing 101. The proximal actuator part 310 of the actuator assembly has an opening 311 at its proximal end configured for a hypodermic needle 204 to extend through when the device 100 is actuated. The proximal actuator part 310 may also comprise further indicia 312 in or on the moulding in order to allow a user to quickly identify the opening 311.

One or more moveable and/or deformable elements may be provided to assist in keeping the device 100 in a primed position. One or more moveable/deformable cantilevers may be used. In the embodiment shown, a pair of cantilevers 110 is disposed at or towards the distal end of the housing 101, on an internal surface. The cantilevers 110 extend longitudinally from the internal distal surface towards the proximal end of the housing 101. Each cantilever 110 terminates in a respective pair of detents: a laterally inwards extending detent 111 and a laterally outwards extending detent 112. The cantilevers 100 are therefore substantially 'T' shaped in cross-section. In embodiments, the cantilevers 110 may be configured differently e.g. 'L'—shaped, or otherwise with a proximal end of the cantilevers having a greater dimension that their distal end. Although two cantilevers 110 are shown, it will be appreciated that just one or more cantilevers may instead be provided. The cantilevers 110 are flexible, deformable and/or pivotable such that their proximal ends 111, 112 are moveable laterally within the housing 101.

The housing 101 further comprises a pair of stop walls 105, positioned towards the proximal end of the device 100, at a fixed distance from the proximal end of the housing 101.

For sterility, a rubber seal 204r may be pressed onto a tip of the needle 204. A non-coring needle may be used to prevent particles of rubber from entering the patient's tissue. A plastic wrapping 204w may be provided to seal the remaining portion of the needle 204.

Figure 3:
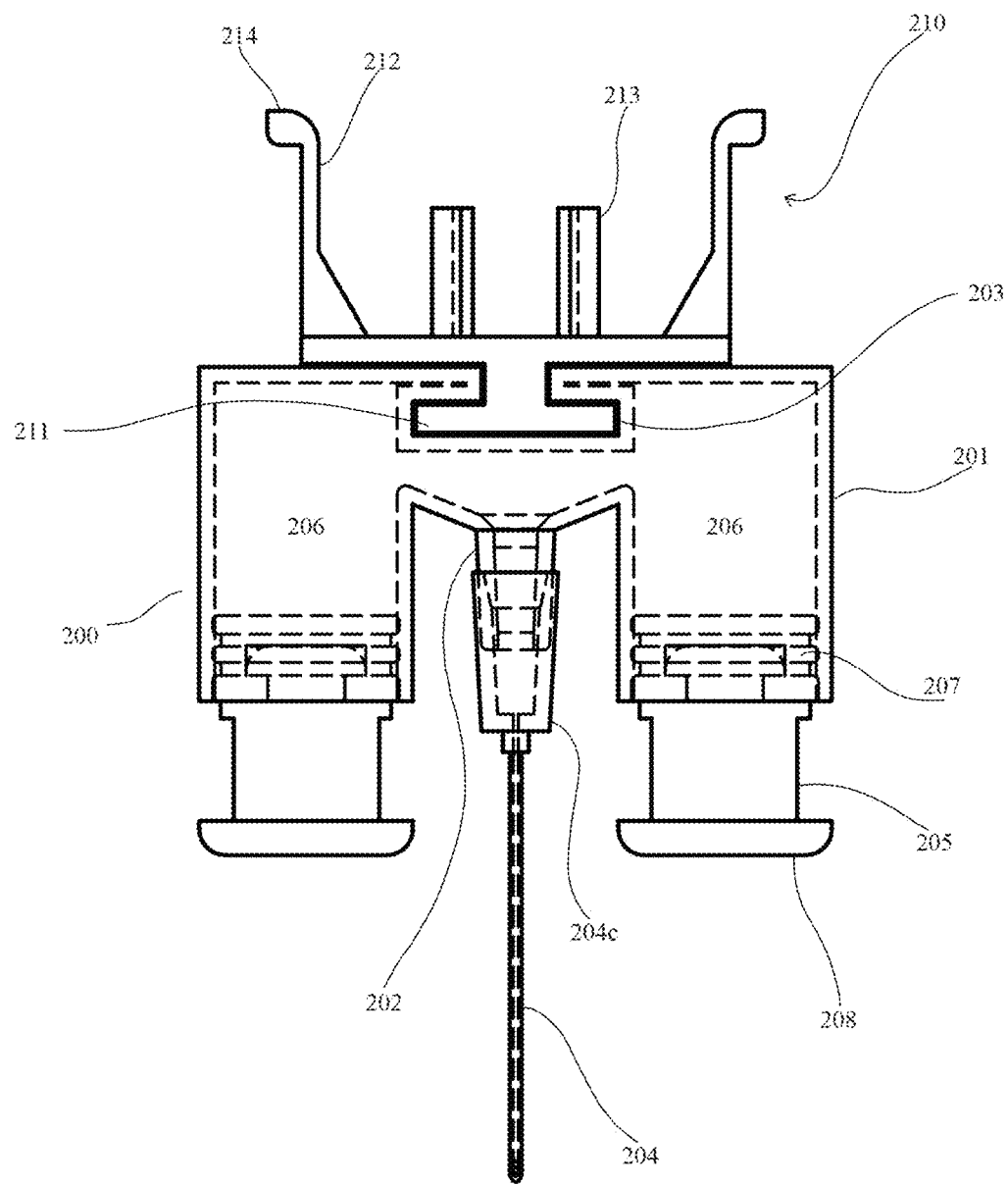
FIG. 3 shows a detailed view of a syringe carrier assembly.

FIG. 3 shows the syringe carrier assembly, which was shown disassembled in FIG. 1, in more detail. The syringe carrier assembly comprises a syringe carrier 210, a syringe 200, the hypodermic needle 204 and a pair of plungers in the form of pistons 205. The proximal end of the syringe carrier 210 comprises a male element 211 that is receivable within a female element 203 provided at the distal end of the syringe 200. In the embodiment shown the male element 211 is a T-shaped protrusion and the female element 203 is a correspondingly shaped aperture or slot.

The needle 204 is attached or is attachable to the syringe 200. The needle 204 comprises a collar 204c. The attachment of the hypodermic needle 204 to the syringe 200 can be achieved by crimping the collar 204c onto a needle attachment point 202 provided on a proximal end of the syringe 200, or may be otherwise secured e.g. via a screw fit, bayonet fit or snap fit etc. The pistons 205 are inserted into or receivable within respective openings of the syringe 200. Each piston 205 may comprise a rigid or hard portion 205a to provide the plunging action and a softer or deformable portion 205b e.g. at least one rubber plunger portion. The softer part 205b provides a sealing means 207 configured to form a seal between the piston 205 and the inner walls of the syringe 200. In the embodiment shown, the soft piston part 205b is configured to be received on the rigid piston part 205a. The soft piston part 205b comprises an aperture or recess 205c to receive a projection 205d of the rigid piston part 205a. The projection 205d may be secured in place within the aperture 205c e.g. by welding, with adhesive or any other suitable known means.

The rigid portion 205a of each piston 205 further comprises an actuation surface 208 at its proximal end. The stop walls 105 of the housing and the plunger support 208 can be corresponding configured to receive the actuation surface 208. In the embodiment shown, the stop walls 105 have a concave configuration and the plunger support 208 has a corresponding convex configuration, but it will be appreciated that different configurations may be used. One or more stabilising projections 205e may be provided towards the distal end of the rigid plunger portion 205a to facilitate stable contact during operation (penetration and injection).

Figure 6:
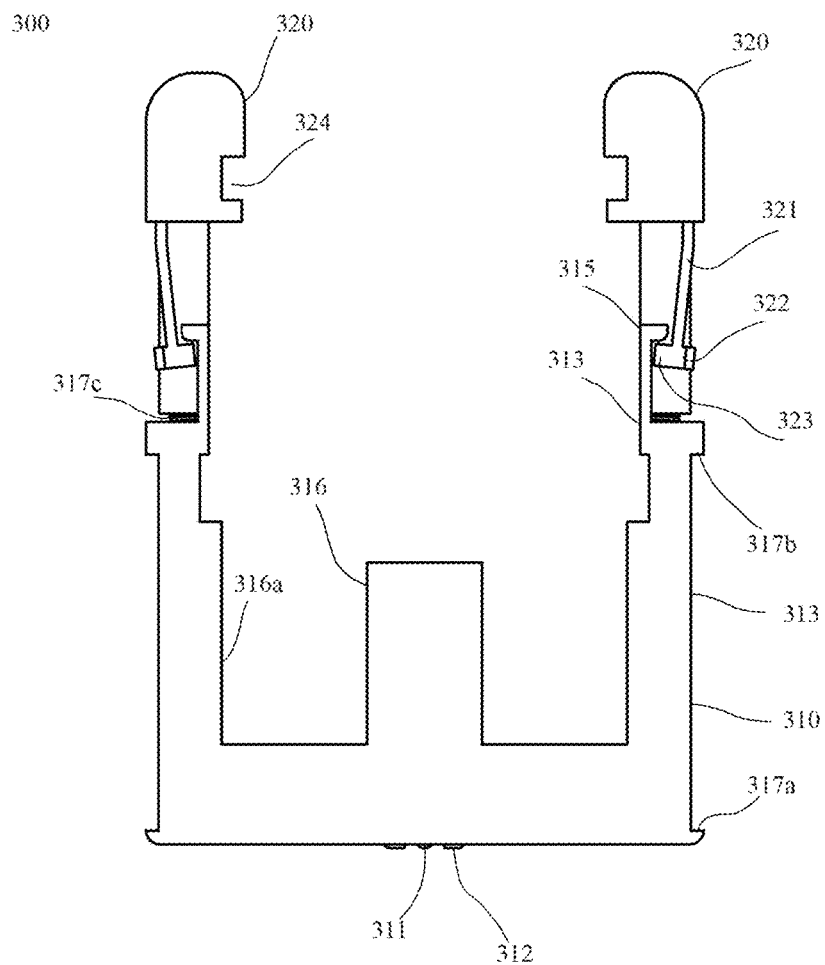
FIG. 6 shows a detailed view of an actuator assembly.

In an embodiment, the soft plunger part 205c may be formed e.g. moulded using medical grade TPE (thermoplastic elastomers), polyisoprene and/or other suitable rubbers. The soft plunger part 205c may have a plurality of ribs, ridges or rings for an enhanced seal within the syringe 200. The shape of the piston 205 and rubber plunger 207 corresponds to the shape of a chamber 206 of the syringe 200. The syringe carrier assembly is configured to translate longitudinally within the housing 101. The protrusions and/or ribs 104 together with walls 316a on the proximal actuator part 310, discussed later with reference to FIG. 6, provide guides for the syringe carrier assembly to move along.

Figure 4:
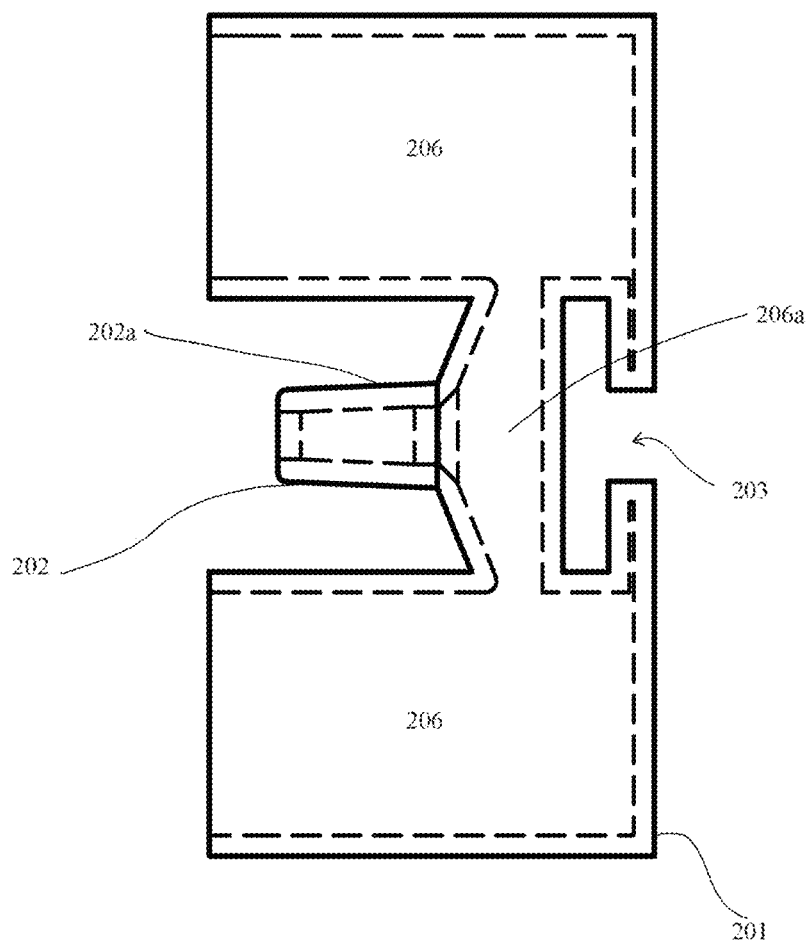
FIG. 4 shows a detailed view of a syringe.

The syringe 200 will now be described in more detail, with reference to FIG. 4. The syringe 200 comprises a vial 201 and the needle attachment point 202. The vial 201 is constructed to have a chamber 206 laterally offset from the needle attachment point 202. This differs from syringes of the prior art which conventionally have any such chambers arranged linearly with a needle attachment point. Offsetting the chamber 206 laterally from the needle attachment point, effectively having them in parallel rather than in series, allows for a reduced longitudinal dimension of the device. Similarly the arrangement of the syringe provides for more effective space utilisation within the housing 101 and, therefore, for a more longitudinally compact housing 101 to be provided.

The vial may comprise one, two, three, four or more chambers. In the embodiment of FIG. 4, the vial 201 comprises a pair of chambers 206. The chambers 206 are arranged symmetrically either side of the needle attachment point 202. Each chamber 206 has a substantially rectangular lateral cross section. The corners of the rectangle are rounded in order to improve the structural integrity of the vial 201 and provide a continuous internal surface for sealing with the rubber plunger 207 and piston 205, as described above. In addition, rounded surfaces provide for better liquid passage and transfer. The lateral cross section of the chambers 206 may vary according to the dimensions of the device 100. Rounded rectangles and discorectangles are an example of a suitable shape, as they are substantially flat whilst having round corners to provide more structural integrity during forming and providing an improved sealing surface for the rubber plunger 207 and pistons 205.

A fluid pathway or channel 206a links, and provides fluid communication between, the pair of chambers 206 and the needle attachment point 202. The fluid pathway may have a small or narrow cross section in the longitudinal direction. The combination of a narrow fluid communication channel 206a, the chamber 206 being offset from the needle attachment point 202 and/or the distal end of the chamber 206 extending beyond the needle attachment point 202 decreases the likelihood of an air bubble being present at or near the needle attachment point 202. This advantageously increases safety during medicine administration. The needle attachment point 202 has a fluid nozzle 202a extending through it in order to provide fluid communication between the vial 201 and the hypodermic needle 204 to be mounted on the needle attachment point 202. The attachment means 203 is provided on or in the vial 201 and is configured to attach the syringe 200 to the syringe carrier 210. The attachment means is formed by the provision of a slot 203 in a wall of the vial 201 as described above.

The vial 201 is constructed from a material to ensure the medication is not contaminated. Medical grade glass (e.g. borosilicate) or plastics can be used. In particular medical grade PP (polypropylene), polyethylene or other suitable material may be used. In a preferred embodiment PP is used. The vial 201 may be formed from two halves and secured e.g. ultrasonically welded together. The vial 201 is configured to contain medication as required for specific/intended purposes. Various compositions may be used dependent on the intended treatment. The device 100 is envisaged, for example, for use in the treatment of anaphylactic shock, in which case epinephrine may be the medication. The device 100 may be used in the treatment of various conditions and the medication specified accordingly. The syringe 200 may be prefilled prior to assembly into the device 100. In other embodiments the syringe 200 may be refillable.

Figure 5:
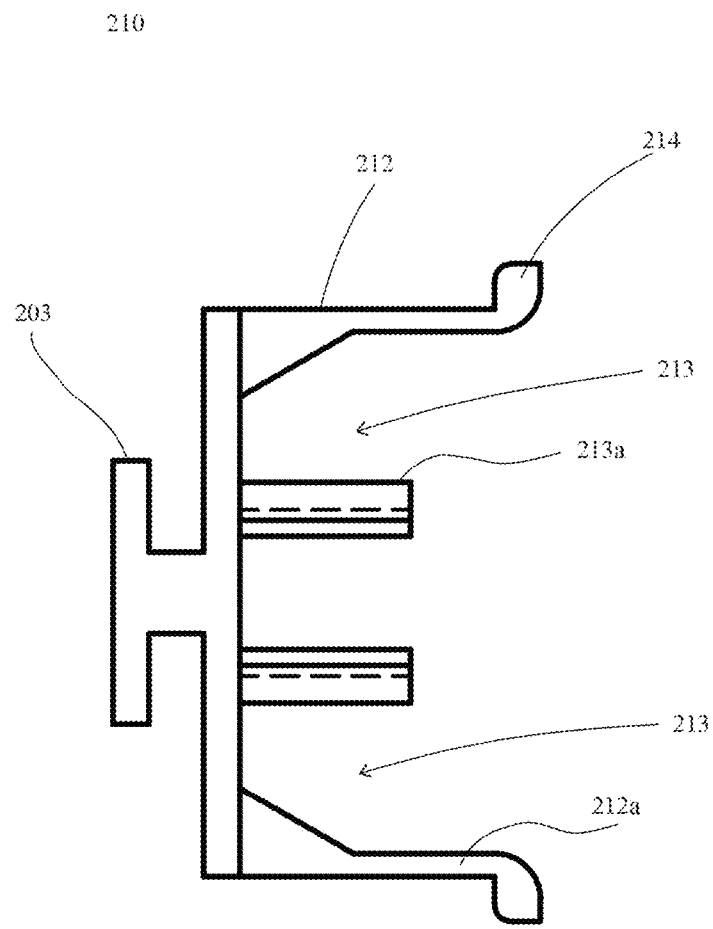
FIG. 5 shows a detailed view of a syringe carrier.

FIG. 5 shows the syringe carrier 210. The syringe carrier 210 comprises attachment means in the form of the protrusion 211. The protrusion 211 is configured to be connectable to the slot 203 of the syringe 200. The slot 203 and protrusion 211 provide the function of moving the carrier assembly down and also keeping the syringe 200 secure in place prior to activation. The carrier 210 further comprises sockets 213 defined by laterally interior walls 213a and laterally external cantilevers 212 or other moveable/deformable engaging means (e.g. alternatives as described above for the cantilevers 110). The sockets 213 are configured to receive the energy storage springs 103. The cantilevers 212 comprise a longitudinally extending arm 212a and a laterally extending detent 214.

Figure 7:
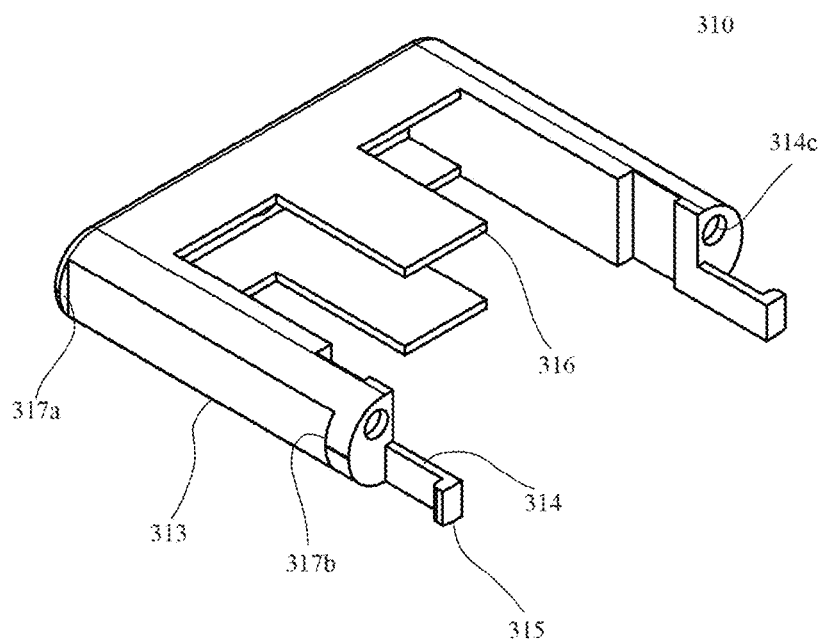
FIG. 7 shows an isometric view of a part of the actuator assembly of FIG. 6.
Figure 7A:
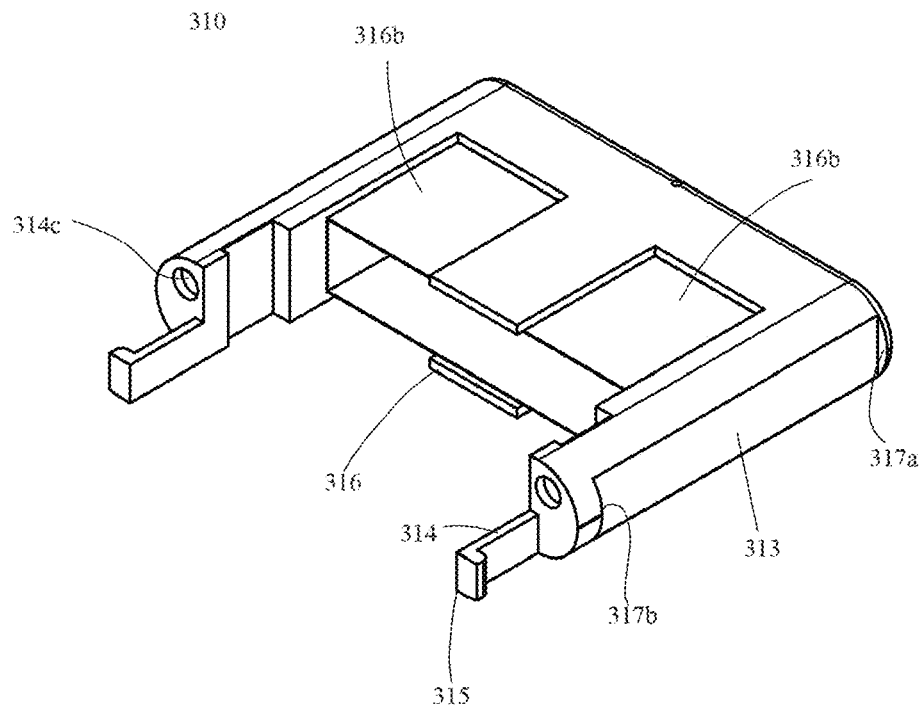
FIG. 7a shows an isometric view of a part of the actuator assembly according to another embodiment.

The actuator assembly is shown in more detail, with the other components removed, in FIGS. 6, 7 and 7a. The actuator assembly comprises a proximal actuator part 310 and a distal actuator part 320. More specifically, the actuator assembly comprises a proximal actuator part 310 and a pair of distal actuator parts 320. The proximal actuator part 310 is the part of the actuator assembly that extends beyond the housing 101 when the cover 102 is removed. The proximal actuator part 310, shown in more detail in FIG. 7, includes a generally flat needle shield 316 at its proximal end and a trailing portion 313, in the form of a pair of arms, extending upwards. A distal end of each arm includes a socket 317c. The distal end of each arm includes a cantilever 314 that is flexibly attached to the arm 313. The cantilever 314 has a laterally outwardly extending detent 315. Each distal actuator 320 has a socket 317c. An actuator spring 330 is housed within and joins the sockets 317c of the proximal part 310 to the sockets 317c of the distal parts 320. In some examples the sockets may contain a boss to retain the spring in place. Each distal actuator 320 comprises a flexibly attached cantilever 321. The cantilever 321 of the distal actuator 320 has a laterally outwardly extending detent 322 and a laterally inwardly extending detent 323. An inwardly facing recess 324 is formed in each of the distal actuator parts 320. Laterally extending detents 317a 317b are formed at the sides and at or towards the proximal and distal ends of the proximal actuator part 310, respectively.

Figure 7B:
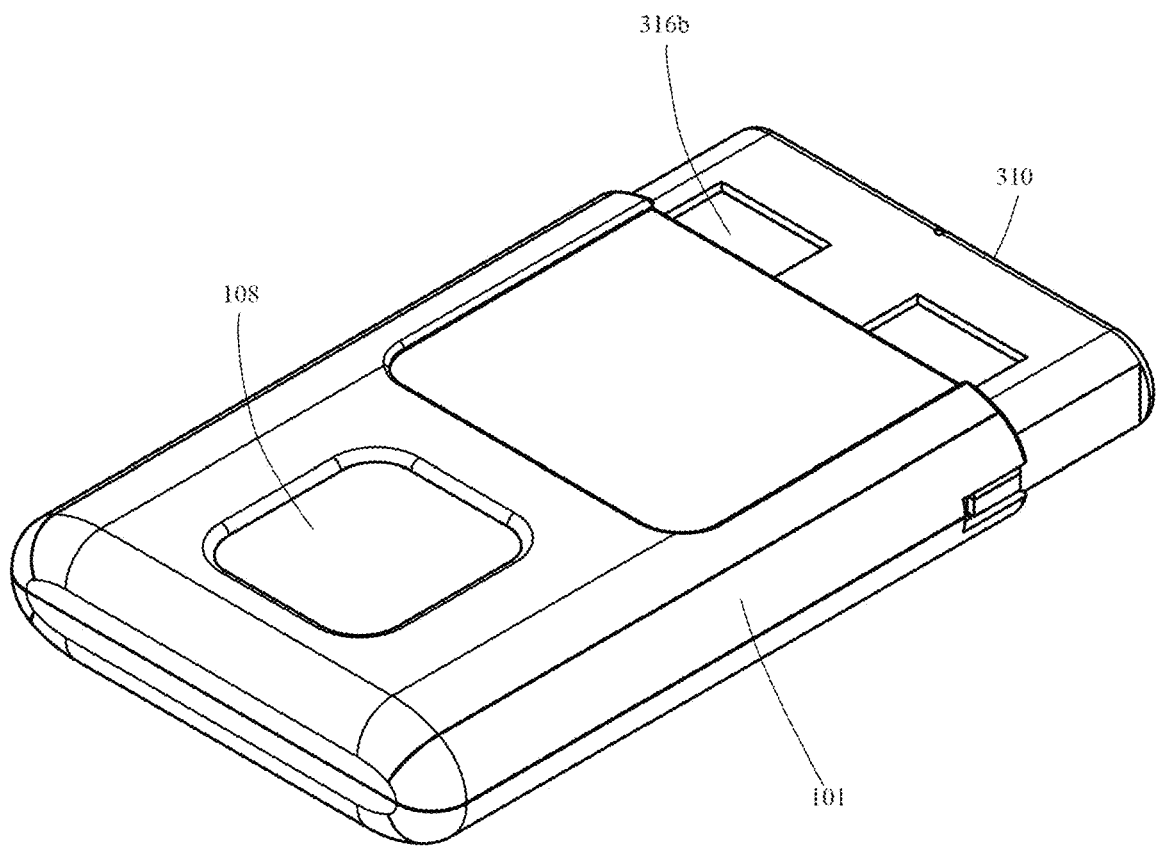
FIG. 7b shows the part of the actuator assembly of FIG. 7a located in a housing.

In the embodiment of FIGS. 6 and 7, the needle shield 316 is a plate that projects longitudinally from the proximal end of the proximal part 310, but does not extends laterally the full width of the proximal part 310. In other embodiments, the needle shield 316 may extend laterally the full width of the proximal part 310. FIG. 7b shows an alternative embodiment similar to that of FIGS. 6 and 7, but where a thin membrane 316b spans the gaps between the needle shield 316 and the arms 313 of the proximal part 310. The membrane may be attached to the needle cover 316 and have an opacity/transparency to help partially or completely block sight of the needle 204 in order to reduce instances of fear. FIG. 7b illustrates how the membrane 316b (or a fully extending needle shield) blocks sight of the needle 204 when the proximal part 310 is extended from the housing e.g. after use.

Figure 2A:
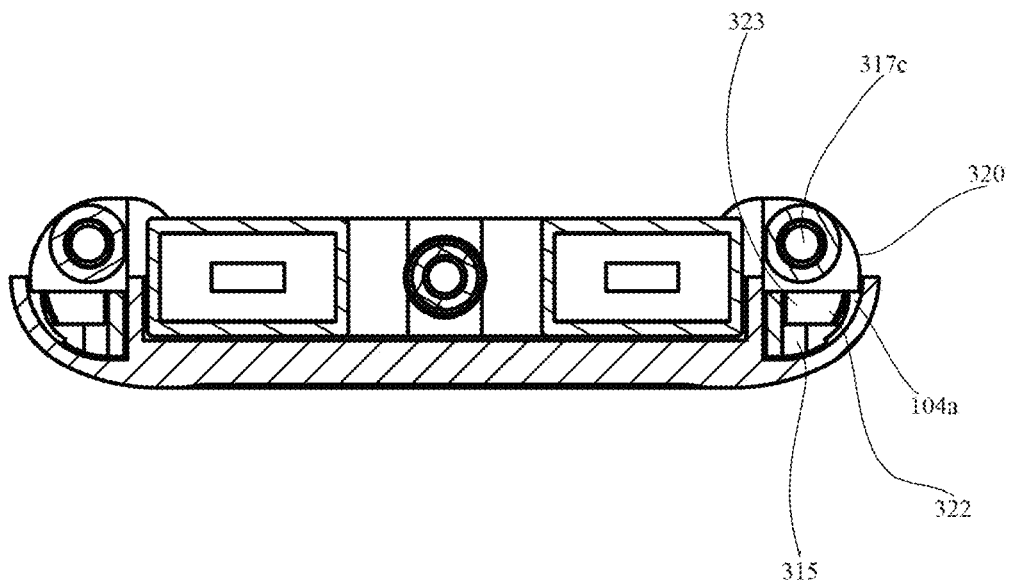

When assembled in the housing 101, as shown in FIG. 2a (and compare with FIG. 8c), a detent 104a, provided in or near the middle of the housing 101 makes the housing 101 too narrow for the laterally outwardly extending detent 322 of the distal actuator part 320. This positioning therefore applies a force and causes the flexible cantilever 321 to bend and its laterally inwardly detent 323 to cooperate with the laterally outwardly extending detent 315 of the cantilever 314 of the proximal actuator part 310.

Figure 10A:
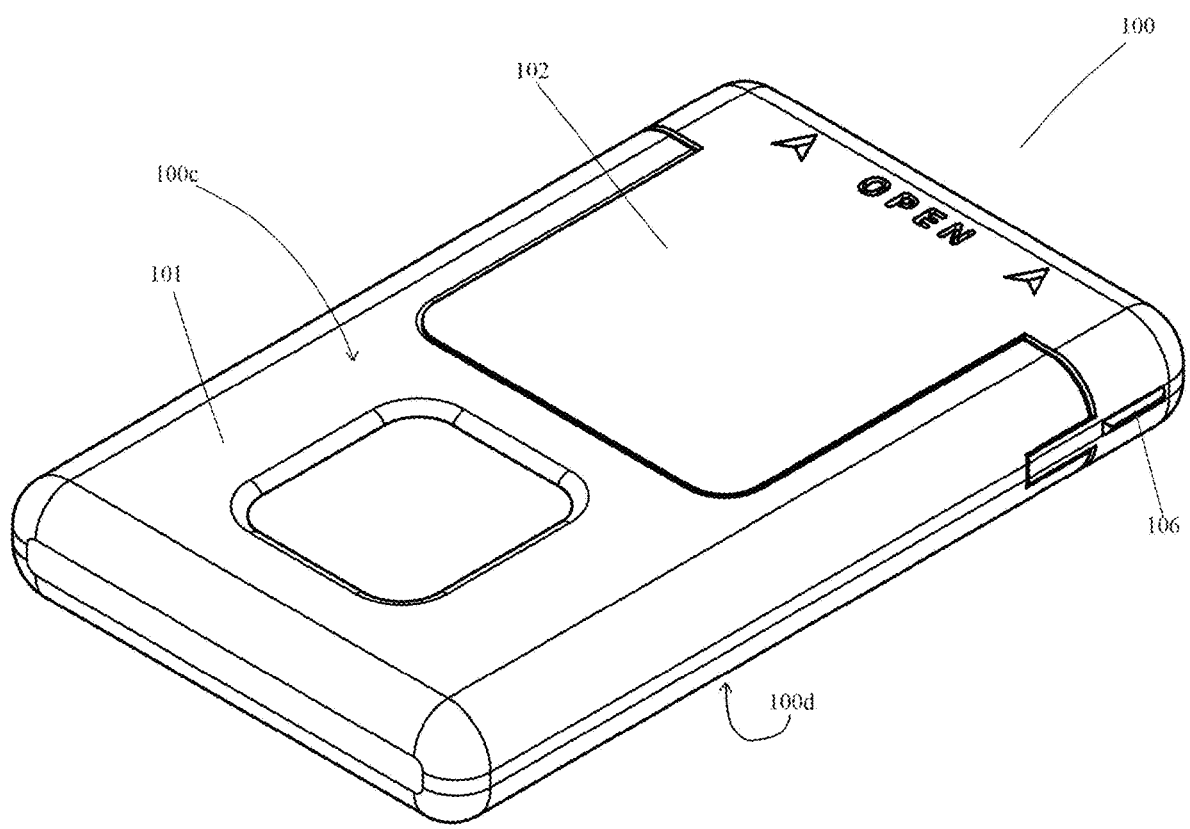
FIGS. 10a and 10b show the exterior of the medication delivery device of FIG. 1 or FIG. 2 fully assembled.
Figure 10B:
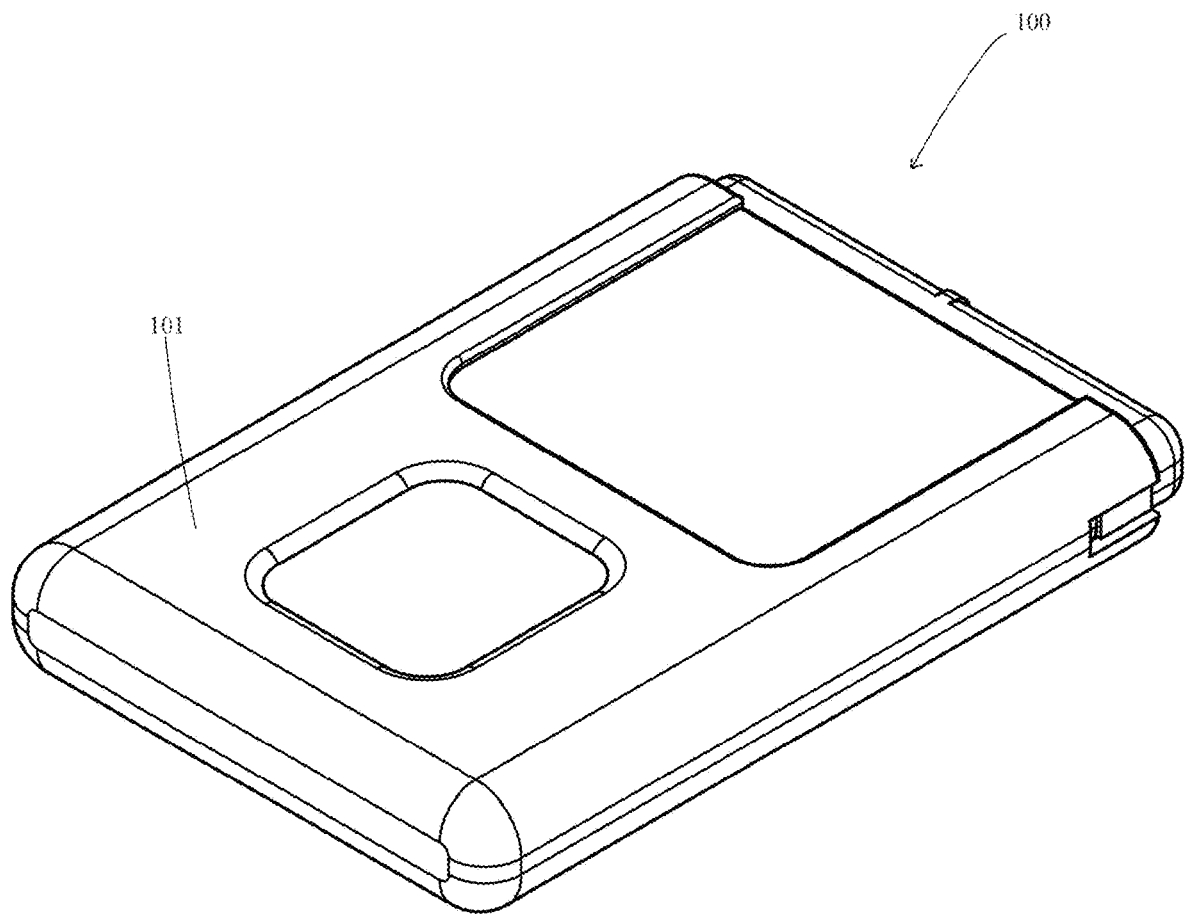

FIGS. 10a and 10b show the medication delivery device fully assembled. It can be seen that the housing 101 and the cover 102 are configured to cooperate with each other and provide a substantially flush exterior surface where they connect. This not only provides for an aesthetically pleasing device, but helps protect the components inside from contamination. When formed from plastic, the housing 101 and 102 can also be sealed via ultrasonic welding.

Figure 8A:
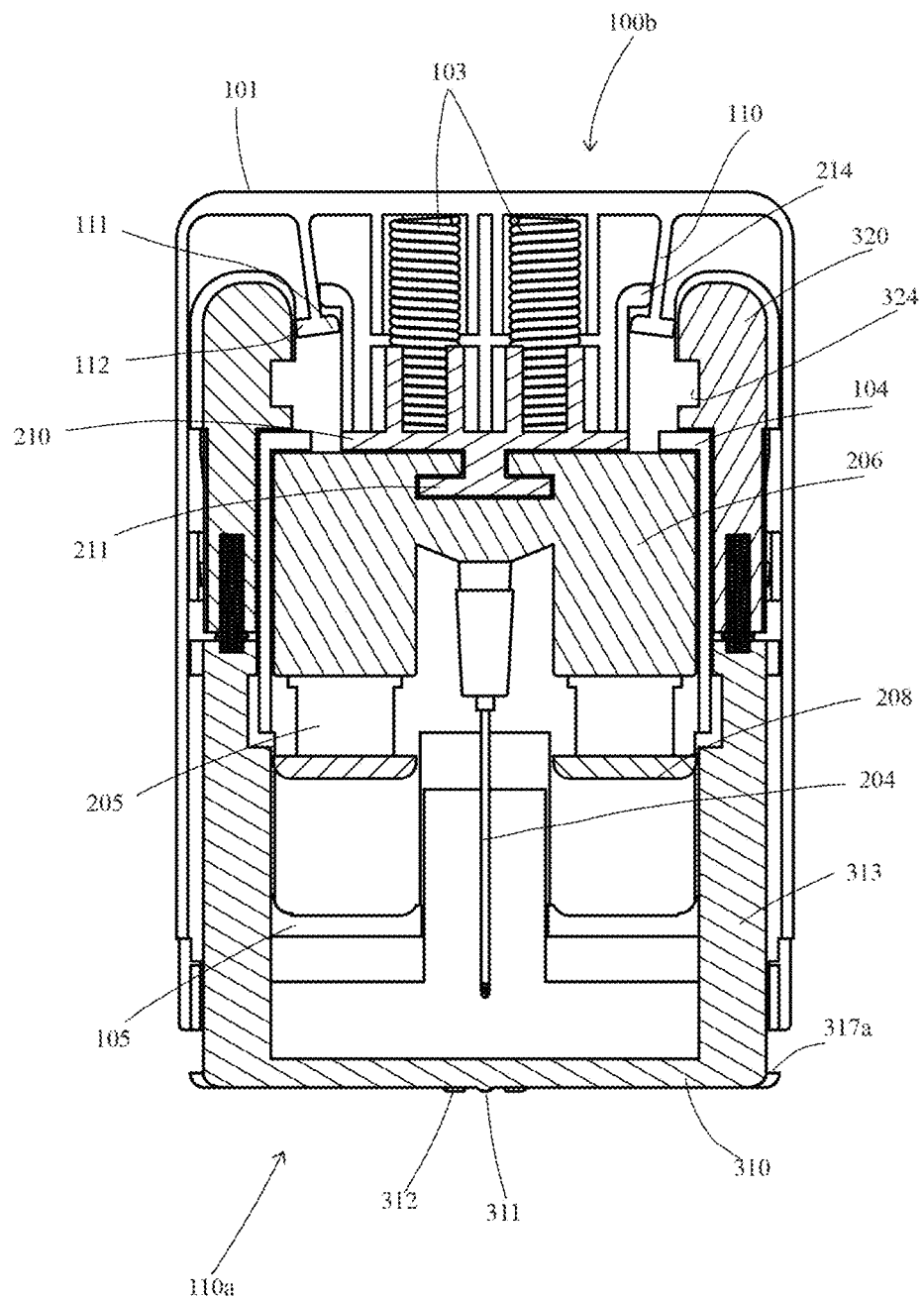
FIGS. 8a-8f show the medication delivery device of FIGS. 1 and 2 through various stages of actuation.
Figure 8B:
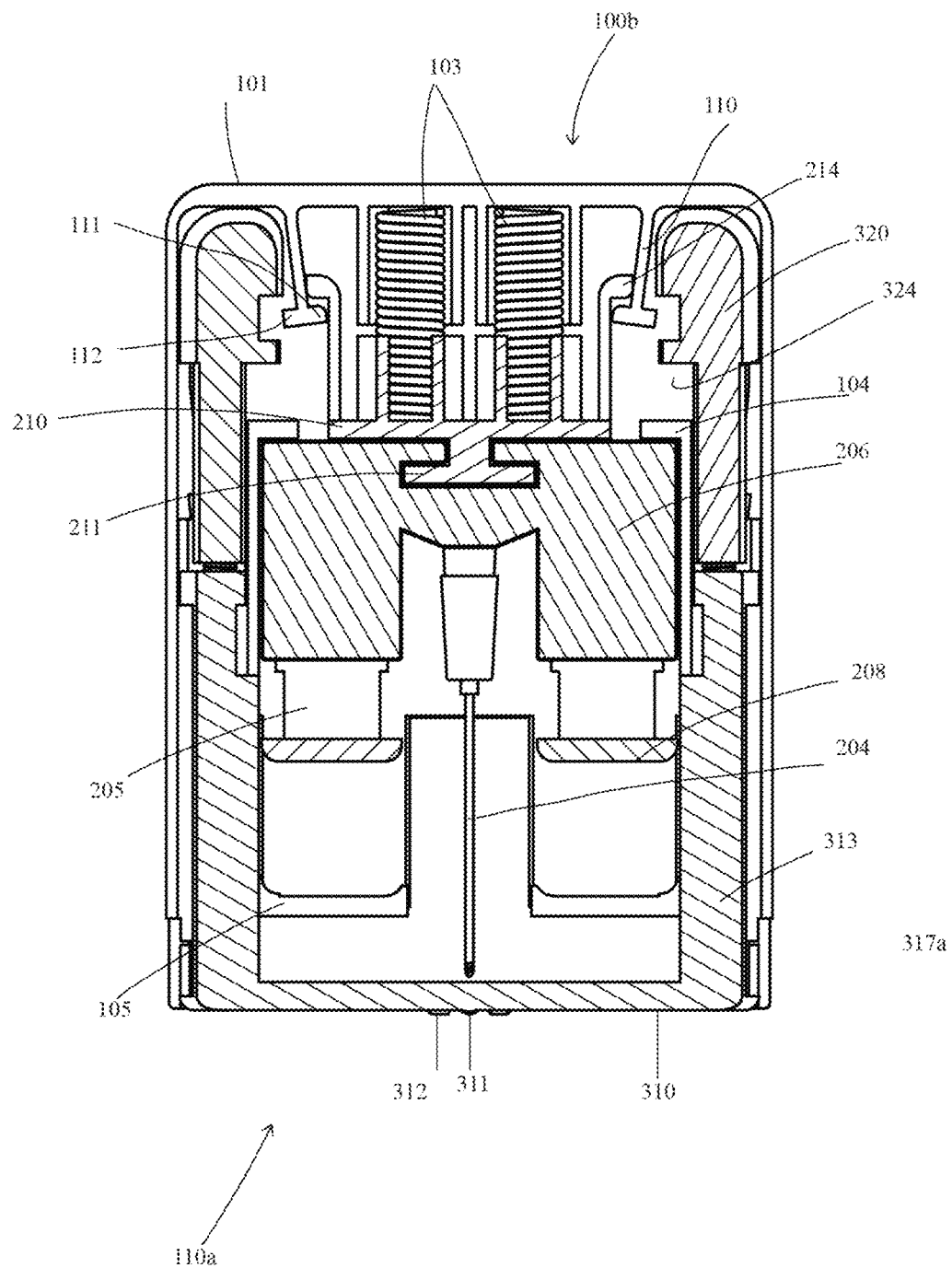
Figure 8C:
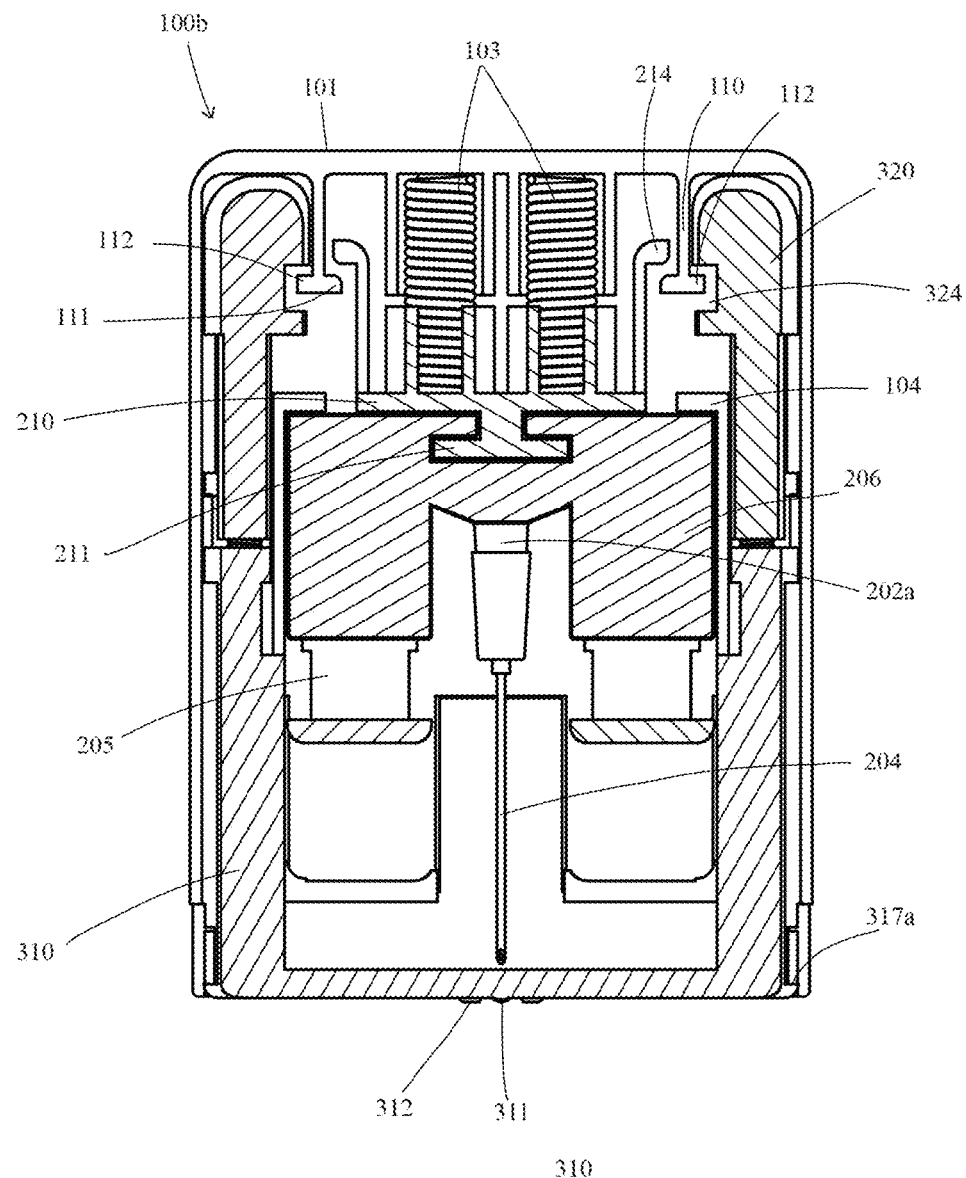
Figure 8D:
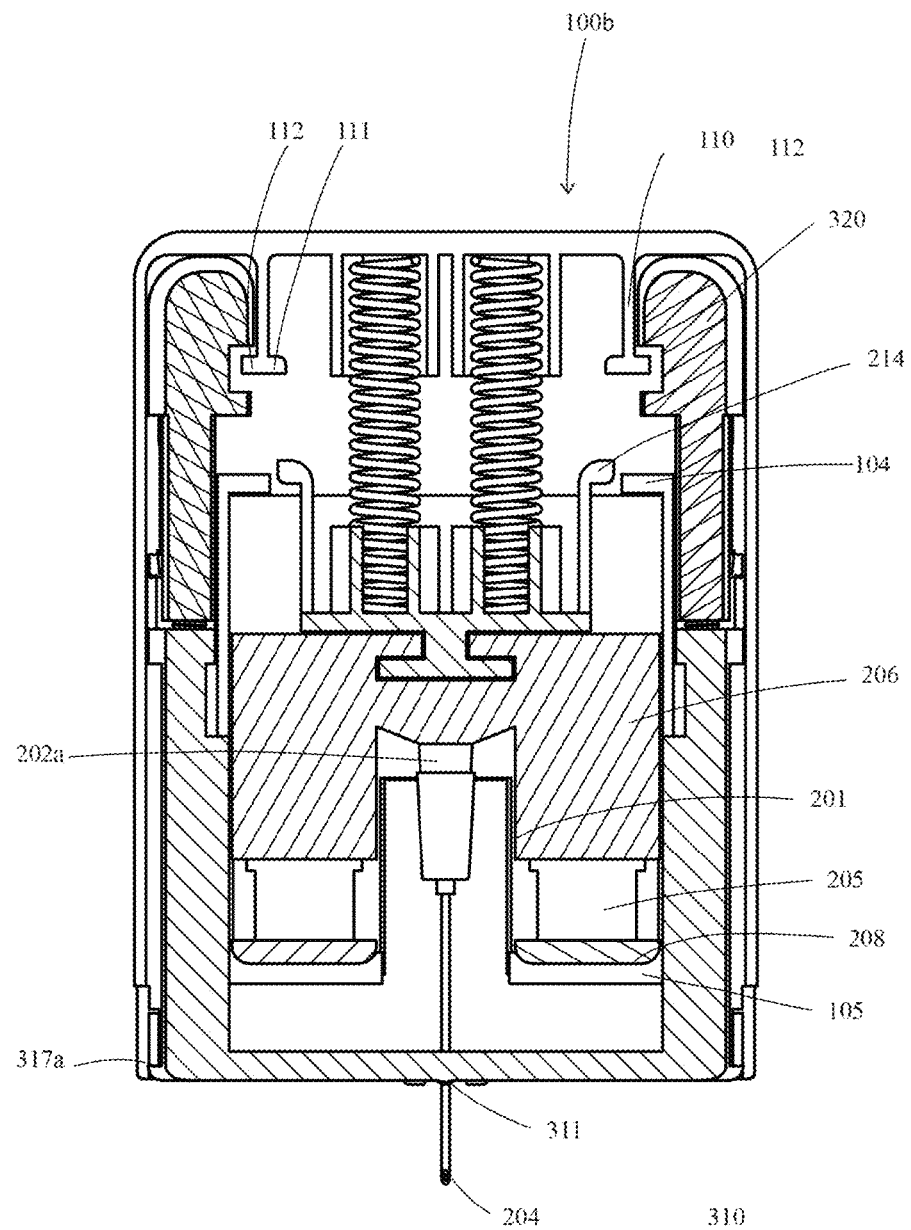
Figure 8E:
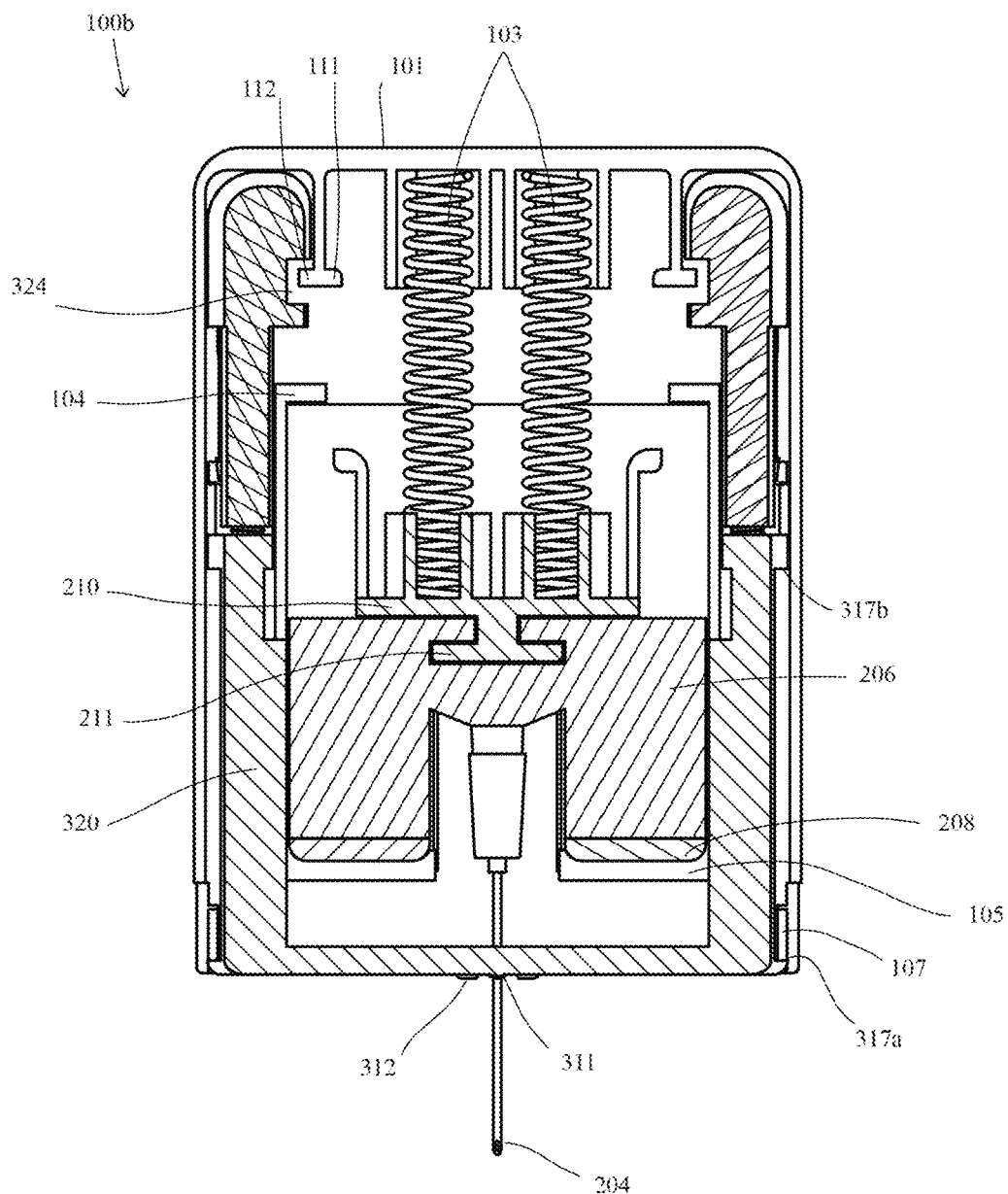
Figure 9A:
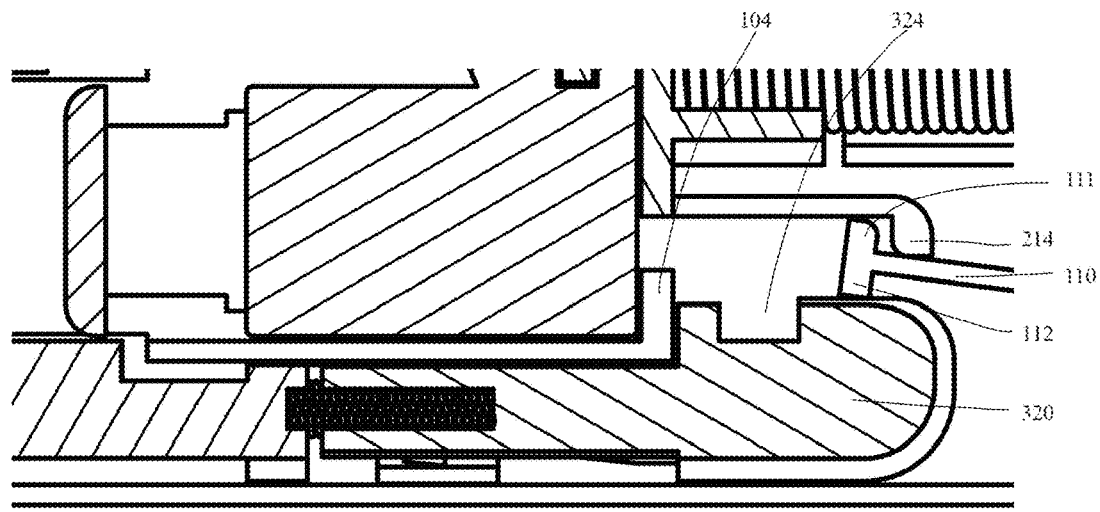
FIGS. 9a-9c show a more detailed view of the actuator assembly during the stages shown in 8a-8e.

Operation of the device 100 will now be described in relation to FIGS. 8a-8e and 9a-9c. FIG. 8a shows the device 100 in its primed form, similar to the device 100 as shown in FIG. 2. FIG. 9a provides a close up of the relevant components of FIG. 8a. The cover 102 has been removed, exposing the proximal actuator part 310. The housing cantilevers 110 are set in a primed position. The housing cantilevers 110 have elastic properties and, in the primed position, are biased from a resting position, which is substantially along the longitudinal direction. In this position the housing detents 111, 112 are trapped between the syringe carrier detents 214 and the distal actuator part 320. The laterally inwardly extending detents 111 of the housing 101 engage with the syringe carrier detents 214 and restrain the syringe carrier assembly, keeping the springs 103 compressed and the energy therein kept stored.

Figure 9B:
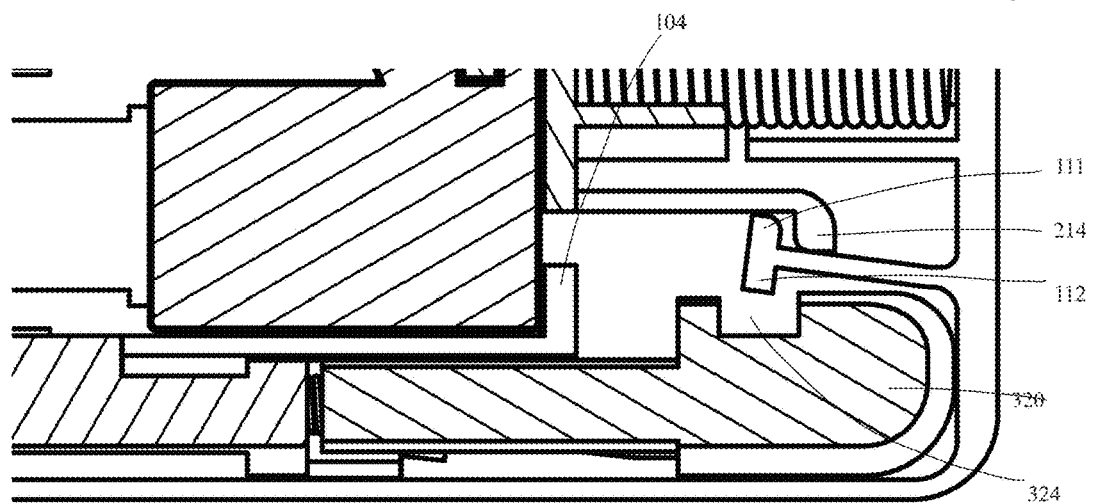
Figure 9C:
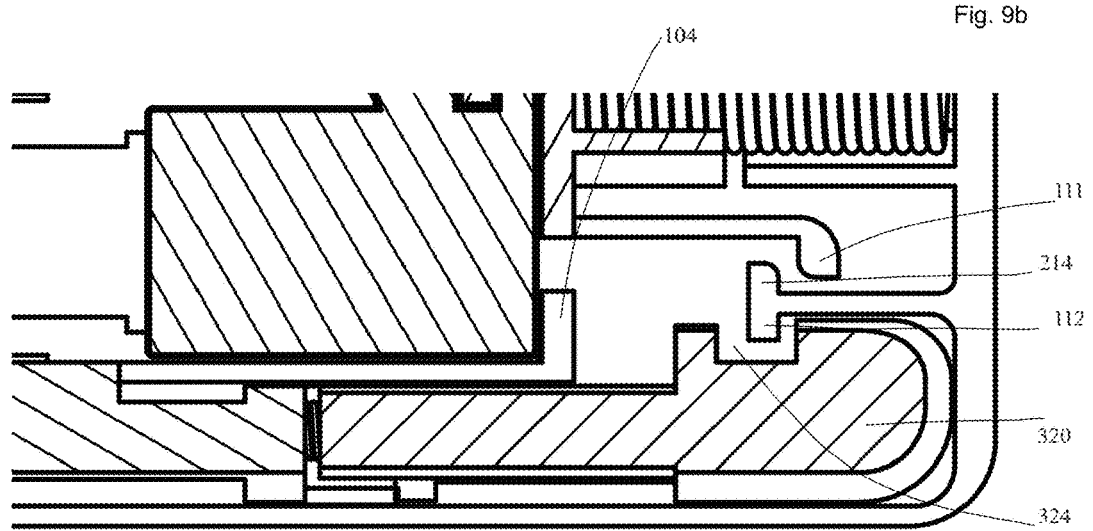

In use, the proximal end of the proximal actuator 310 is pressed against an injection site of a patient. This action translates the actuator assembly longitudinally, further into the housing 101, as shown in FIGS. 8b and 9b. This reduces the distance between the point of the needle 204 and the opening 311, thus providing a reduced travel distance required for the needle 204 to penetrate the skin of the patient. In this position the housing detents 112 are freed from contact with the distal actuator part 320 so they can extend into the recesses 324 of the distal assembly 320. I.e. the housing cantilevers 110 are freed, and allowed to rotate further into their relaxed positions, as shown in FIGS. 8c and 9c. This action releases the housing detents 111 from the syringe carrier detents 214, allowing the syringe carrier assembly linear freedom of movement between the distal and the proximal ends of the housing. Furthermore, the force causing compression between the proximal and distal actuator parts is released and the corresponding detents of actuator parts 315, 323 are no longer held in a state of cooperation (compared with the cooperated state shown in FIG. 6).

With the housing detents 111 no longer restraining the syringe carrier assembly, the energy storage springs 103 are operable to extend from their biased or compressed state, thereby releasing at least some of their stored energy to assist propelling the syringe carrier assembly towards the proximal end of the device 100. As shown in FIG. 8d, this causes the needle 204 to extend beyond the proximal end of the housing 101, through the opening 311. With the proximal end 100a placed against the injection site of the patient, the needle 204 will puncture the skin and penetrate the injection site. As the syringe carrier assembly moves from the distal end to the proximal end, the plunger supports 208 come into contact with the stop walls 105. This stage of the actuation sequence can therefore be termed a penetration stage.

The springs 103 continue to extend and the syringe carrier assembly continues to be forced towards the proximal end 100a of the device 100. With the plunger supports 208 braced by the stop walls 105, this movement has the effect of causing the pistons 205 to be pushed into the vial 201. More accurately, the vial 201 is pushed in a proximal direction around the pistons 205. As the pistons 205 move into their respective chambers 206 the volume capacity for fluid within the vial 201 decreases. This increases the pressure within the vial 201 which in turn forces the medication through the fluid nozzle 202a of the needle attachment point 202, into the needle 204 and from there into the tissue of the patient. This stage can therefore be termed an injection stage. The open ends of the syringe 200, the length of the pistons 205 and/or the vial 201 volume, can be configured according to a required medication dosage. The injection movement also causes the needle 204 to further extend deeper into the tissue up to a desired length. The desired length is dictated by the longitudinal sizes of the components controlling how far the proximal actuator part 310 can extend into the housing 101. Separating the actuation movement into two stages allows the plungers 205 to be situated in what would otherwise be an unutilised void within the housing 101 which contributes to the device's compactness. Furthermore, since there is no component touching the plunger body 208 prior to activation there is no danger of movement pre-releasing the medicine. This means that the device 100 unconventionally uses soft rubber plungers 205b instead of conventional harder rubbers that have higher friction in order to resist movement. Therefore, a more compact spring 203 can be used to push the piston 205 and rubber plunger 205b in the proximal direction for administering medicine, providing less energy than would conventionally be required. Having the two stages in series further allows for a single energy storage means (albeit split into parallel springs in the present example) to provide both the penetration force required as well the force required to create the pressure in order to inject the medication.

The device 100 is held, pressed against the patient's body, for a period of time. The indicia 108 may specify a recommended time, which may be in excess of the time needed for the device 100 to fully activate and the vial 201 to be evacuated. The period of time that the device 100 should be pressed against the patient's body should be according to medical advice specific to the medicine solution used in a given application. For example, even when considering epinephrine, some manufacturers in the market specific to hold the device for 5 seconds while others 10 seconds. By way of a practical example, the device of the present invention can fully complete the administration of a 0.5 ml dose in approximately 3 seconds. The indicia 108 may therefore indicate a minimum time operational time of at least three seconds, maybe 4, 5, 6 or a longer time of 7 seconds or more in order to ensure full delivery of the medication. FIG. 8e shows the device 100 with the needle 2014 fully extended e.g. it represents the fully penetrated position.

Figure 8F:
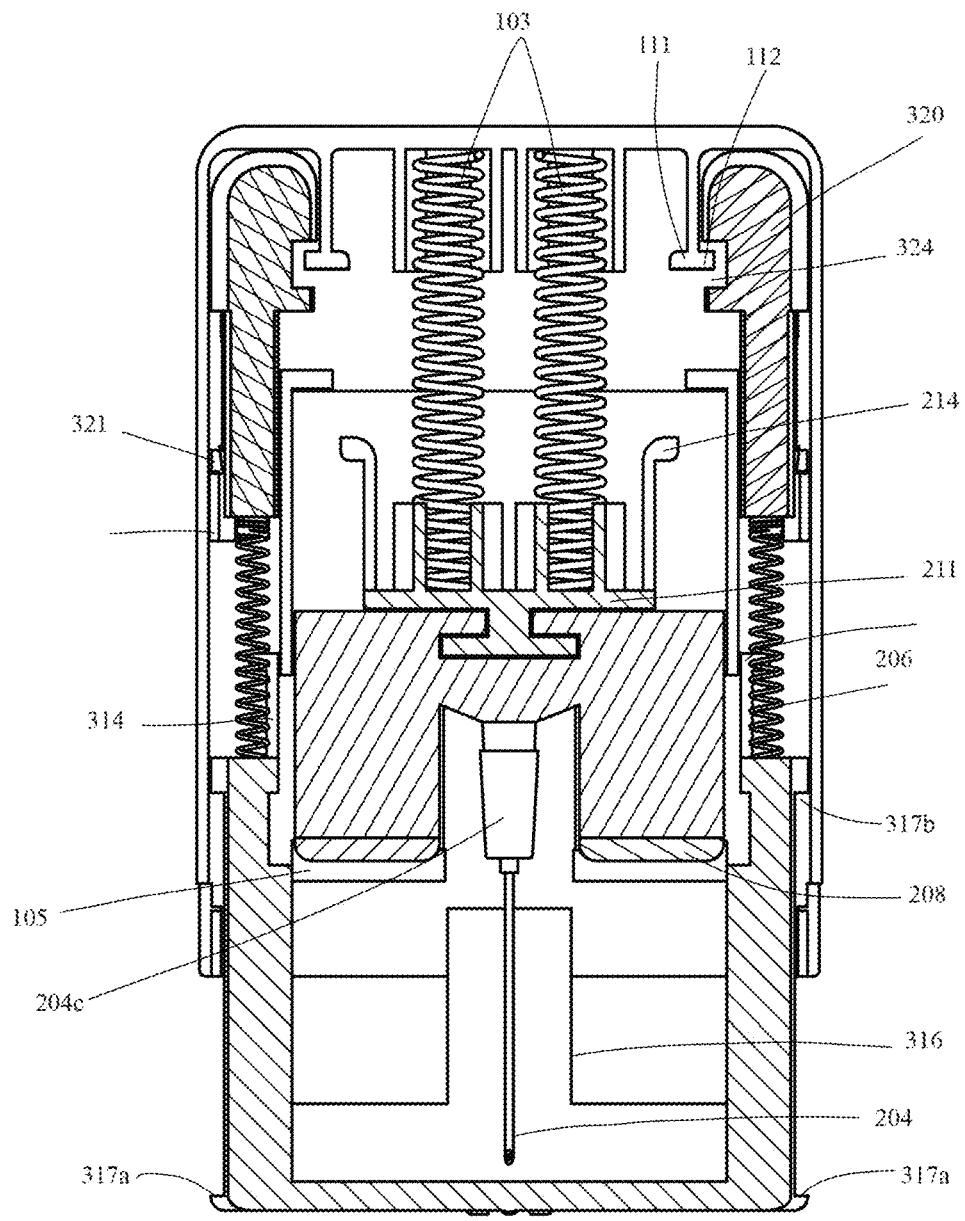

Once the activation is complete, and the medication is delivered into the patient, the device 100 is operable to be removed so as to extract the needle 204 from the patient. The device 100 can be slowly pulled back, away from the patient, withdrawing the needle 204 from the injection site. With the proximal end 100a of the actuator assembly no longer pressed against the injection site surface the proximal actuator part 310 is free to translate longitudinally outwards until 317b comes into contact with 107 and is braced against it. This stops it from extending out beyond a desired length. As described above, the proximal actuator part detent 315 is no longer engaged with the distal actuator part detent 323, the respective cantilevers 314, 321 having rotated to their resting (unbiased) positions. This is illustrated in FIG. 8f.

Figure 11A:
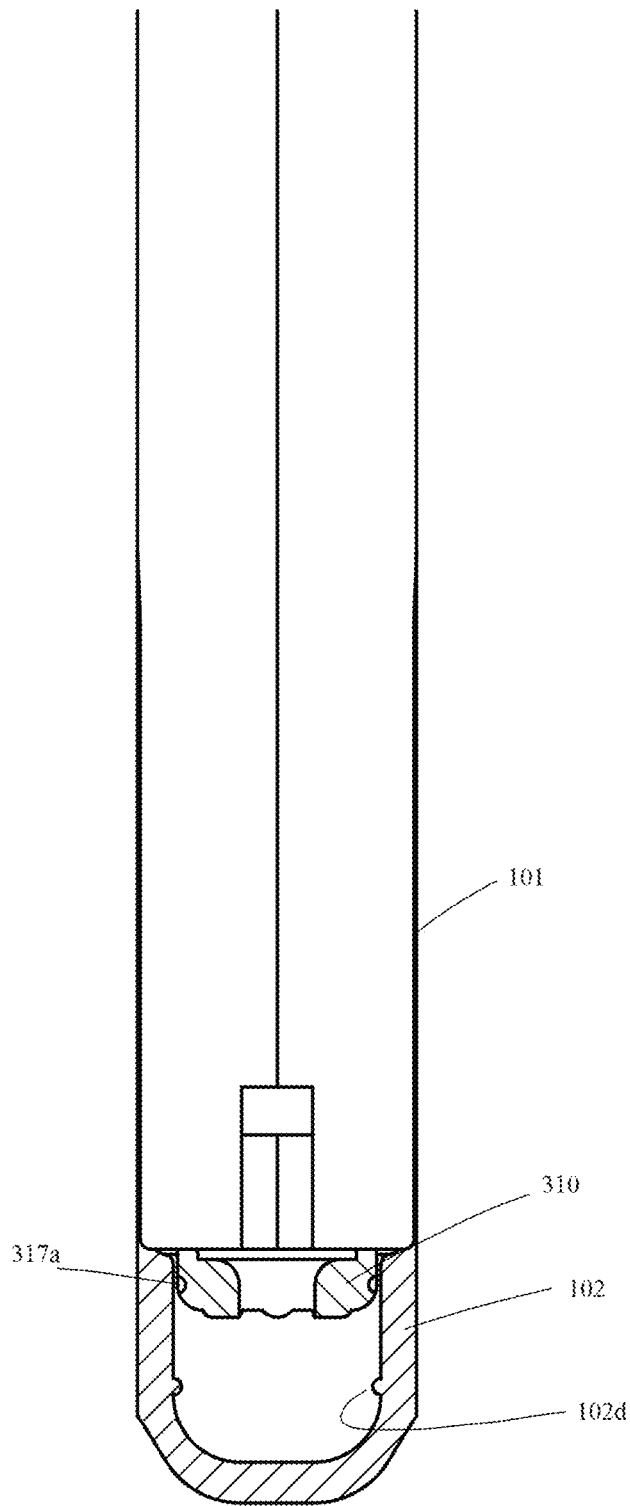
FIGS. 11a-11c show a cutaway section of the device of FIG. 1 or FIG. 2 at different stages.
Figure 11B:
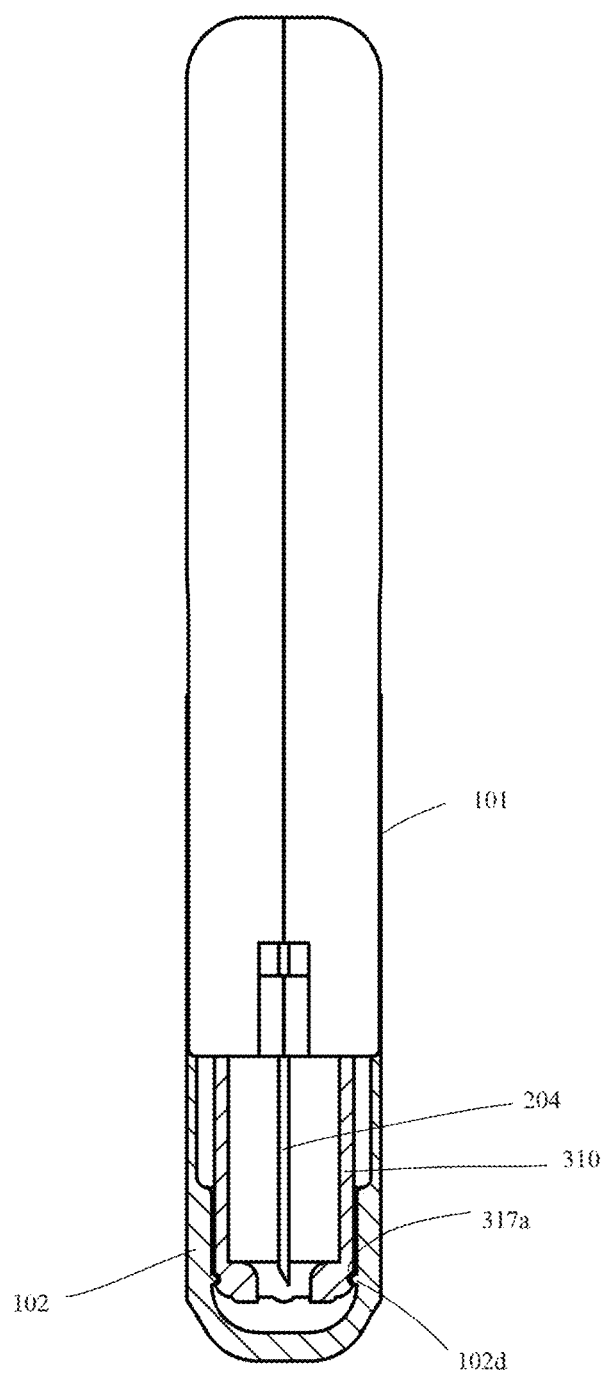
Figure 11C:
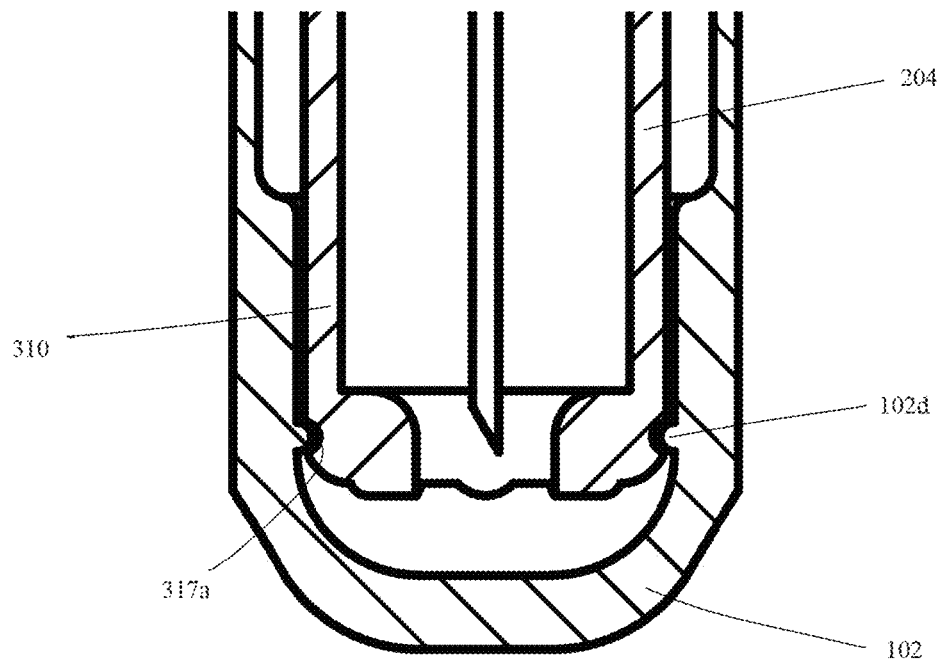

The actuator assembly springs 330 force the proximal actuator part 310 out to a predetermined length. The length is determined by the distance between 317b and 107 and should be designed to be sufficient to re-encompass the needle 204, thereby reducing the biohazard risk associated with having the used needle 204 exposed. Excessive translation of the proximal actuator part 310 is prevented through the side detents 317b coming into contact with the proximal housing detents 107. This results in a width that is less than the width of 317b of the actuator. In this embodiment, the cover 102 will no longer be able to secured into the original recessed housing 101d after the device 100 has been fired due the energy of springs released. However, internal detents 102d are provided that are configured to mate with the proximal detents 317a on the proximal actuator part 310. FIG. 11a shows the device 100 before use, with the cover 102 and proximal actuator part 310 in section view, with the cover 102 secured in the recessed housing 101d. The detents 102d and 317a are not in contact at this stage. FIG. 11b, and FIG. 11c which is a close up of the proximal end of FIG. 11b, shows the device 100 after use, with the cover 102 secured by the detent 102d of the cover engaged with the detent 317b of the proximal actuator part 310.

Various modifications, designs, examples and embodiments may be provided that fulfil the same function as the described embodiment. Various releasable attachment means between the actuator parts may be used. Other energy storage means may be applied. Parts described as having male/female interactions can be interchanged. Features and components provided in one part of the device or syringe may instead be used in another part of the device or syringe.

Figure 12:
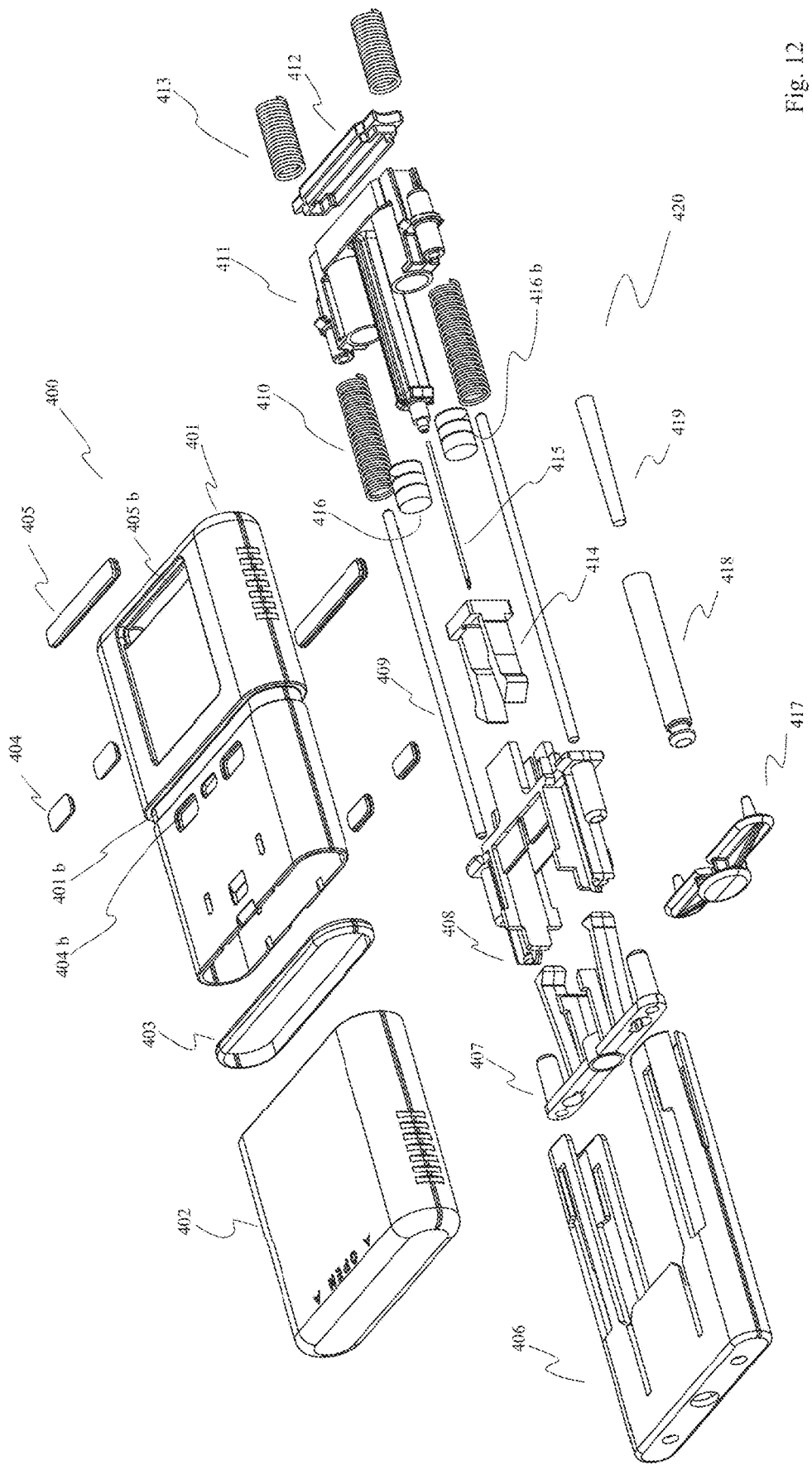
FIG. 12 shows an exploded view of another medication delivery device.

FIG. 12 is a further such embodiment of a medication delivery device 400 and shows, in an exploded view, multiple interconnectable or interconnected parts. An outer periphery of the medication delivery device 400 is defined by a housing 401 and a cover 402. A seal 403 is provided that fits into a seal groove 401b of the housing 401. One or more first windows 404 are provided that fit into one or more respective first window apertures 404b of the housing 401. One or more second windows 405 are provided that fit into one or more respective second window apertures 405b of the housing 401. The first windows and their respective apertures are smaller than the second windows and their respective apertures. An actuator 406 and chassis 408 are provided. The actuator 406 is functionally similar to the proximal actuator part 310 of the preceding embodiments and the chassis 408 is functionally similar to the distal actuator part 320 of the preceding embodiments. A delivery subassembly 420 that fits within the housing 401 and cover 402 comprises the actuator 406 and the chassis 408. The delivery subassembly 420 further comprises a majority of the components of the medication delivery device 400. The function of the components of the delivery subassembly 420 is described in more detail below. The components of the delivery subassembly 420 include one or more of: an actuator lock 407 that that is configured to fit inside the actuator 406, one or more guide rails 409, a chassis lock 414, one or more actuator springs 410 (shown in compressed configuration) and one or more vial springs 413 (shown in compressed configuration), a vial 411, a vial cover 412, one or more plungers 416 (the plungers comprising optional sealing ridges 416b), a hypodermic needle 415 which is sharpened at its proximal end, a needle cover 418, a needle liner 419 and a safety plug 417.

Figure 13:
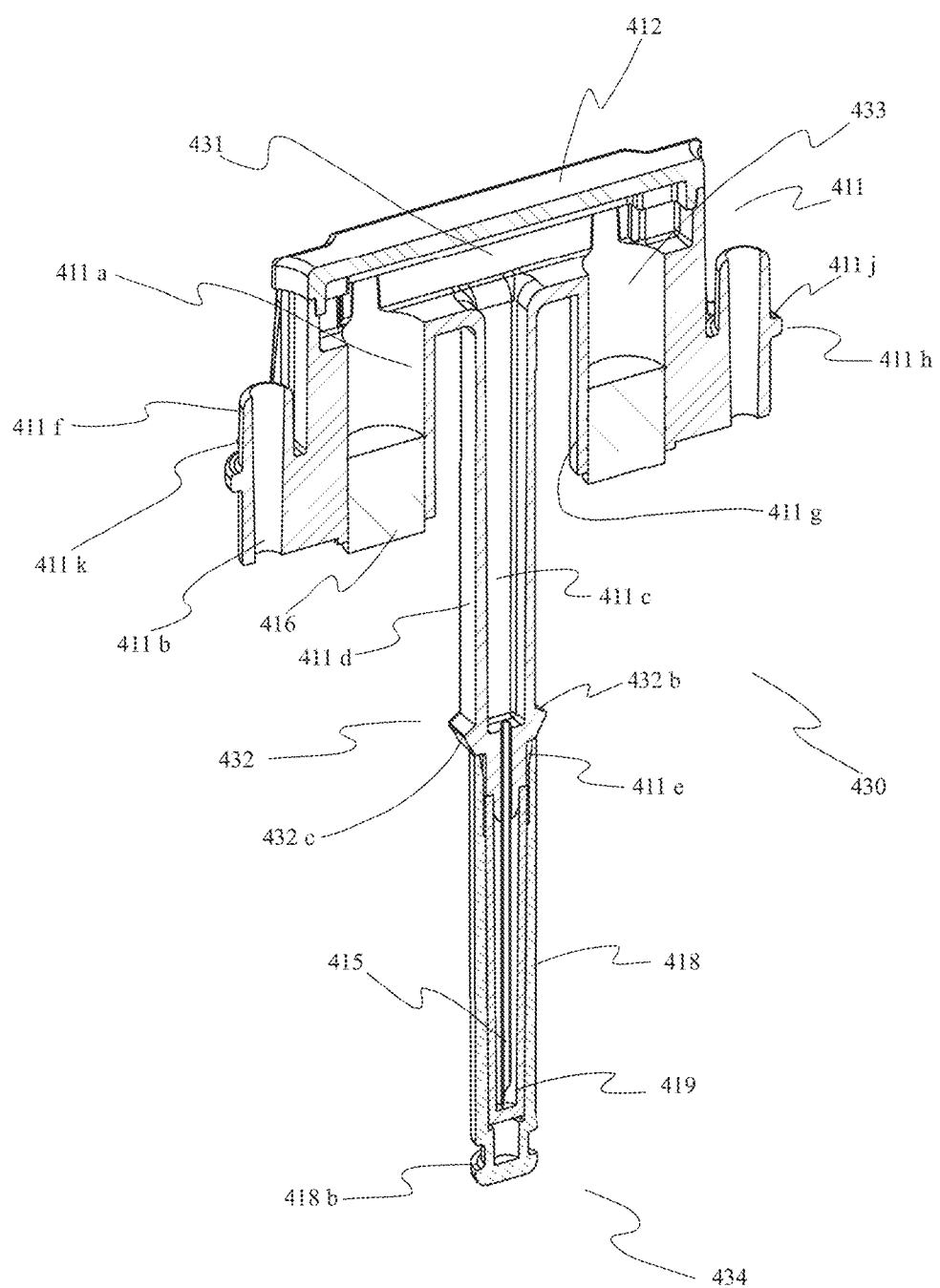
FIG. 13 shows a cross section of a vial subassembly of the medication delivery device of FIG. 12.

FIG. 13 shows a half section of a syringe 430 comprising the vial 411 with the vial cover 412. In this embodiment, the vial 411 and the vial cover 412 may be formed from a polymer such as polypropylene, cyclic olefin copolymer or any other material (including borosilicate glass as described in relation to other embodiments) that is suitable for a medicament 433. The vial cover 412 is attached to the vial 411 by welding, bonding or similar industry standard means such that a liquid-tight seal is achieved. The vial 411 comprises a hollow, elongated central section 411d with a closed proximal end. A distal end of the hypodermic needle 415 is connected to the closed proximal end of the elongated central section 411d e.g. by welding, bonding, luer lock, threaded attachment or over moulding such that a liquid-tight seal is achieved between the hypodermic needle 415 and the vial 411. A continuous fluid connection is provided between the vial central cavity 411c and the bore of the hypodermic needle 415. The proximal end of the central section 411d has one or more vial catches 432 protruding from it. Each vial catch 432 has a vial catch upper face 432b and a vial catch lower face 432c, and a seal surface 411e that extends in the direction of hypodermic needle 415. The vial 411 has two cylinders 411g having bores 411a spaced apart symmetrically on either side of the central section 411d. The bores 411a are chambers and are analogous to the chambers 206 of the previous embodiments. Plunger 416 can be inserted into the proximal end of each bore 411a and is free to slide within it towards the distal end with sealing ridges 416b ensuring a liquid-tight seal. Laterally offset outwardly from each cylinder 411g is an outer vial guide 411h with one or more vial clips 411k (more visible in FIG. 17), a vial spring post 411f, vial spring platform 411j and a vial guide rail bearing 411b. The vial guide rail bearing 411b is configured to be slidably connected to the guide rail 409. The guide rail 409 and vial guide railing therefore provide an analogous function to the attachment means between the syringe and the syringe carrier of the previous embodiments. The vial top cavity 431 connects the central cavity 411c and the bores 411a forming a contiguous volume within which the free flowing medicament 433 is stored. As plungers 416 move from the proximal end to the distal end of bores 411a, the medicament 433 is pressurized and forced out through the hypodermic needle 415. A needle cover subassembly 434 comprises the rigid needle cover 418. A needle liner 419, preferably formed from a pliable material such as an elastomer, is provided within the rigid needle cover 418. The needle liner 419 is attached or is attachable e.g. bonded, over moulded or held by friction or mechanical means into a needle cover groove 418b. The needle cover groove 418b is formed at a proximal end of the needle cover 418. The needle cover subassembly 434 covers the exposed length of the hypodermic needle 415. The distal end of the needle liner 419 fits tightly over the seal surface 411e at the proximal end of the vial central section 411d. The needle cover subassembly 434 is firmly held by the tight fit to the vial 411, but can be detached by pulling it off. The needle cover subassembly 434 is configured to maintain sterility of the hypodermic needle 415 by the needle liner 419 fitting tightly over the seal surface 411e.

Figure 14:
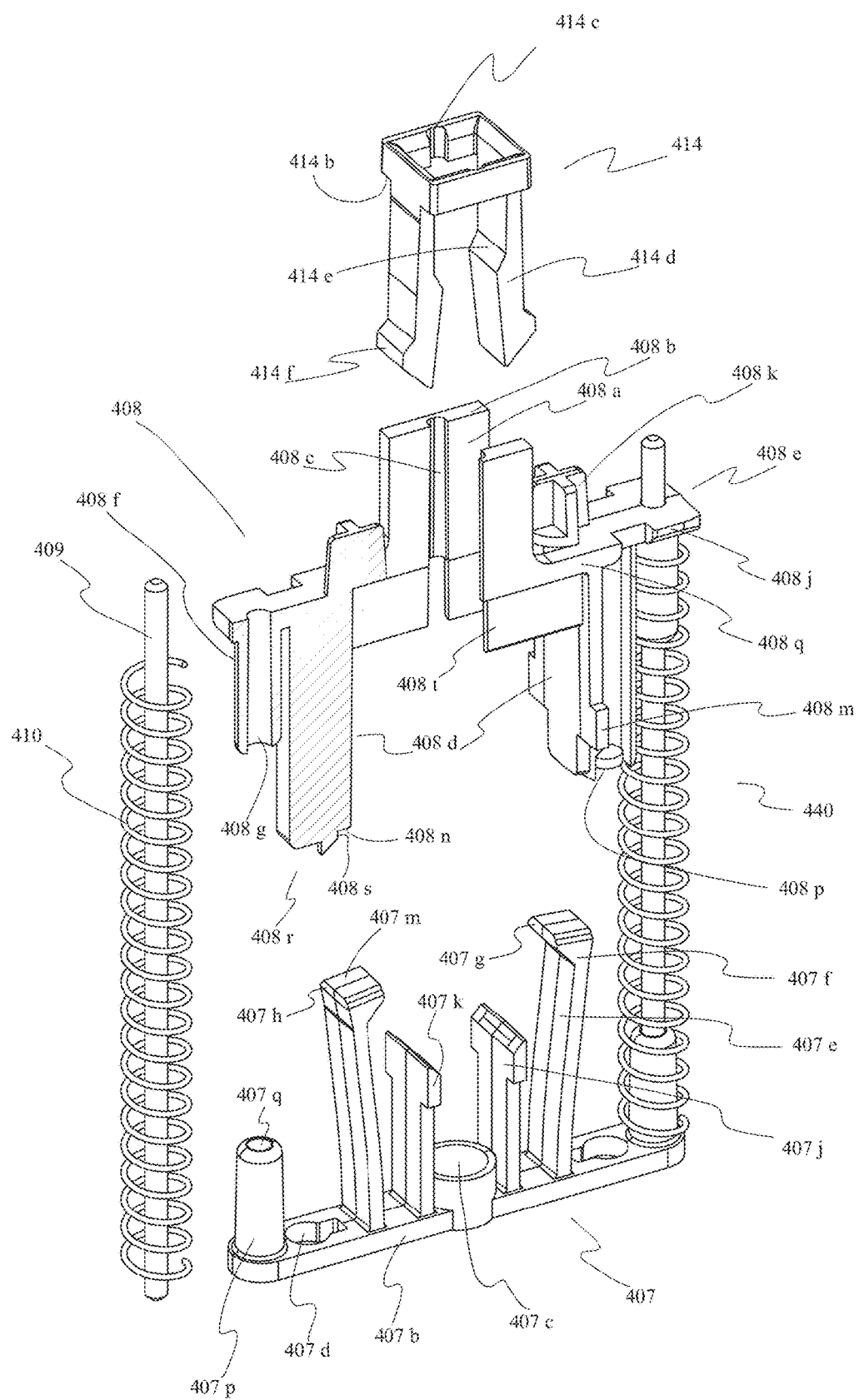
FIG. 14 shows a partial sectional view of a chassis subassembly of the medication delivery device of FIG. 12.

FIG. 14 shows the chassis subassembly 440 of the medication delivery device 400, with a partial section through the chassis 408, and the chassis lock 414, one of the guide rails 409 and one of the actuator springs 410 offset for clarity. The chassis lock 414 has a distal end and a proximal end. One or more longitudinal upper guide grooves 414c are provided at the distal end in a frame of the chassis lock 414. The chassis lock 414 has a lower surface 414b, the lower surface 414b being a surface of the frame of the chassis lock 414 facing the proximal end. One or more chassis tabs 414d extend from the lower surface 414b to the distal end. The chassis tabs 414d are made from an elastically deformable material such as acetal. The chassis tabs 414d have an inner stop face 414e and an outer stop face 414f. The elasticity of the chassis tabs 414d allows a pair of symmetrical tabs, as shown in FIG. 14, to have inner stop faces 414e and outer stop faces 414f that can move closer together and further apart as the chassis 414d tabs are flexed together or apart. While the chassis lock 414 is shown in this embodiment as a separate component to chassis 408, it is an option to combine the two together into one part and they may be formed as a unitary component. The chassis 408 has a chassis central platform 408q with one or more chassis upstands 408a at its distal end. Each chassis upstand 408a has a chassis upper face 408b configured to abut against chassis lock lower surface 414b to locate the chassis lock 414. One or more centre guide grooves 408c extends longitudinally through upstands 408a and is aligned with upper guide grooves 414c. Central platform 408q supports one or more plunger pushers 408k that fit within bores 411a. The plunger pushers 408k may be of cruciform shape as shown, solid, or any other configuration that can push plunger 416 inside bore 411a. Outboard of plunger pushers 408k are chassis spring platforms 408e that include a chassis spring post 408f, over which the actuator spring 410 can fit, with a chassis guide rail bearing 408g within it, through which the guide rail 409 may slide. Each chassis spring platform 408e has one or more chassis clips 408j projecting from it. Each chassis spring platform 408e has a chassis extension 408r extending to the proximal end of the chassis 408. At the proximal end of each chassis extension 408r, is a chassis extension lock face 408n, a chassis extension stop face 408s, one or more chassis assembly protrusions 408m and a chassis assembly face 408p. One or more chassis reinforcement plates 408t are provide to improve the stiffness of chassis central platform 408q. Actuator lock 407 is formed from an elastic material such as acetal and consists of an actuator lock platform 407b with a central needle hole 407c through it and one or more actuator lock safety holes 407d through it. Extending from the actuator lock platform 407b is one or more actuator lock arms 407e which have an arm lock 407f at the distal end on which an arm lock inner stop face 407g and an arm lock outer stop face 407h are provided. The elasticity of the actuator lock arms 407e allows a pair of symmetrical arms, as shown in FIG. 14, to have inner stop faces 407g and outer stop faces 407g that can move closer together and further apart as the actuator lock arms 407e are flexed together or apart. Extending from the actuator lock platform 407b is one or more actuator needle guides 407j which have one or more actuator needle guide protrusions 407k at the distal end. Extending from the actuator lock platform 407b is one or more actuator spring posts 407p, which have an actuator lock spring hole 407q through it into which a guide rail 409 can be inserted and firmly held by friction or equivalent means.

Figure 15:
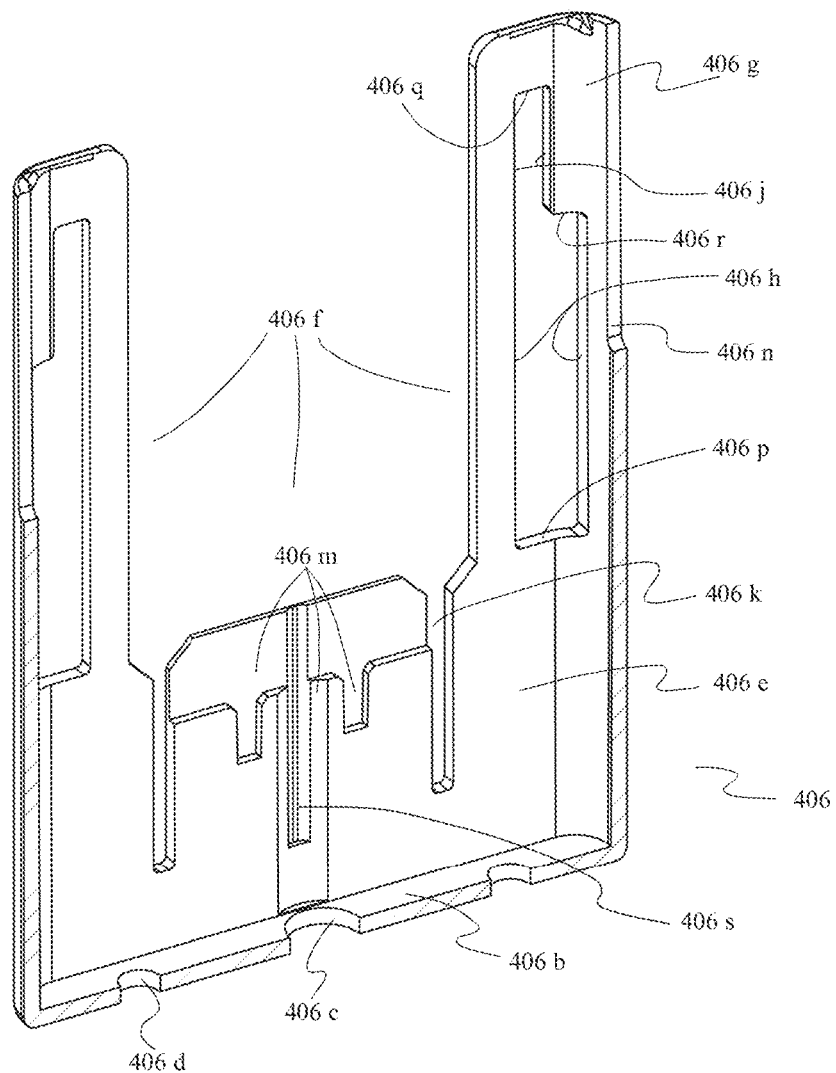
FIG. 15 shows a cross section of an actuator of the medication delivery device of FIG. 12.

FIG. 15 shows a half section of the actuator 406 of the medication delivery device 400 with an actuator base plate 406b at the proximal end containing an outer needle hole 406c and one or more safety cover pin holes 406d. Extending from the perimeter of the actuator base plate 406b is an actuator wall 406e that extends towards the distal end. A central cut-out region 406f leaves two actuator upstands 406g through which further cut-outs form a wide guide 406h at the proximal end terminating in a wide face 406p and a narrow guide 406j at the distal end terminating in a narrow face 406q. An intermediate face 406r is present at the point at which the wide guide 406h and the narrow guide 406j meet. One or more chassis relief slots 406k are cut through the actuator wall 406e and clearance recesses 406m are provided in the actuator wall 406e for the actuator needle guide protrusions 407k, the actuator lock platform 407b and the chassis reinforcement plates 408t. A lower guide groove 406s extends longitudinally in line with the centre guide grooves 408c and upper guide grooves 414c. Strain relief slots 406n are provided in the distal ends of the actuator upstands 406g, to allow the front and back sections of the actuator upstands 406g to stretch apart slightly.

Figure 16:
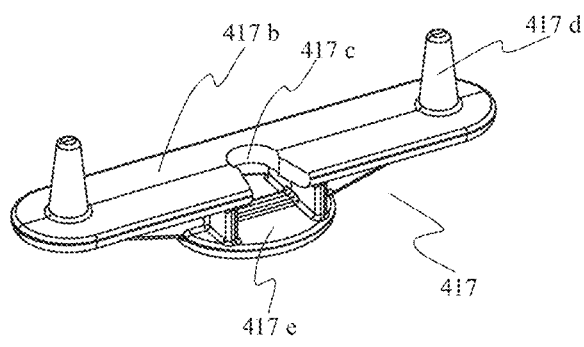
FIG. 16 shows a safety cover of the medication delivery device of FIG. 12.

FIG. 16 shows the safety plug 417 that consists of a safety plug platform 417b with a safety slot 417c in it that can clip securely onto the needle cover groove 418b. One or more safety plug pins 417d extend from the upper face of safety plug platform 417b, and a finger grip 417e extends from the lower face.

Figure 17:
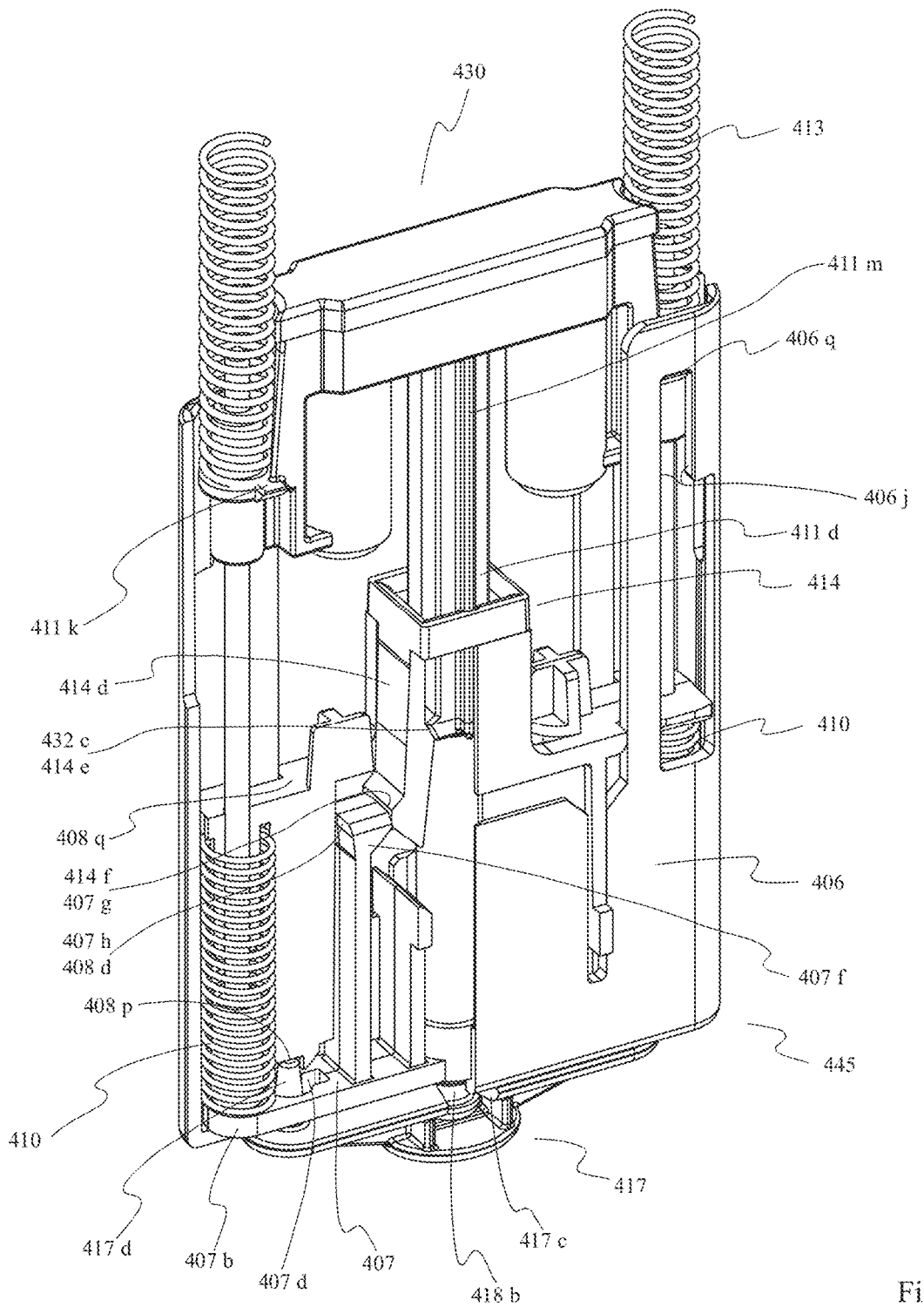
FIG. 17 shows an internal assembly of the medication delivery device of FIG. 12.

FIG. 17 shows an internal assembly 445 of the vial subassembly 430, chassis subassembly 440, actuator 406, vial springs 413, and the safety cover 417 of the medication delivery device of FIG. 12 with a partial section through the actuator and chassis. One or more longitudinal guide ribs 411m along vial central section 411d run freely through upper guide grooves 414c, centre guide grooves 408c and lower guide grooves 406s. The compressed actuator springs 410 exert an expansion force between the chassis central platform 408q and the actuator lock platform 407b. This expansion force pushes the actuator lock 407 against the actuator base plate 406b and thereby pushes the actuator 406 in the same direction. As the vial subassembly 430 is retained inside the actuator 406 via vial clips 411k, which protrude into narrow guide 406j and rest against narrow face 406q, the vial subassembly 430 is also pushed in the same direction as the actuator 406. Movement of the vial subassembly 430 due to the expansion force of compressed actuator springs 410 is however resisted as the vial central section 411d passes through the distal end of the chassis lock 414 and the vial catch lower face 432c rests against the inner stop face 414e of the chassis lock 414 and the chassis lock lower surface 414b rests on the upper faces 408b of the chassis 408. It can also be seen that the outer stop face 414f of chassis tab 414d is touching arm lock inner stop face 407g of arm lock 407f and arm lock outer stop face 407h is touching inner chassis extension face 408d. In this way, the arm lock 407f blocks the chassis tab 414d and prevents it from springing open to allow the vial catch 432 to pass through the chassis lock 414, which allows actuator spring 410 to expand. This is the locked position of the actuator 406 and vial subassembly 430 relative to the chassis 408. Safety plug 417 is shown in its assembled position with the safety slot 417c engaged with needle cover groove 418b. Safety plug pins 417d pass through safety cover pin holes 406d (see FIG. 15) and actuator lock safety holes 407d so that their distal ends make contact with chassis assembly face 408p. In this assembled position, if any force pushes safety plug 417 towards actuator 406, the force would be transferred directly to chassis 408 and actuator 406 would not be influenced. If a force acted on safety plug 417 in a direction away from the actuator 406, for example by a person's fingers pulling on finger grip 417e, the combined safety plug 417 and needle cover subassembly 434 would pull away from the vial subassembly 430 to expose the hypodermic needle 415 and also remove the aforementioned protection against a force being applied to the actuator 406.

Figure 18:
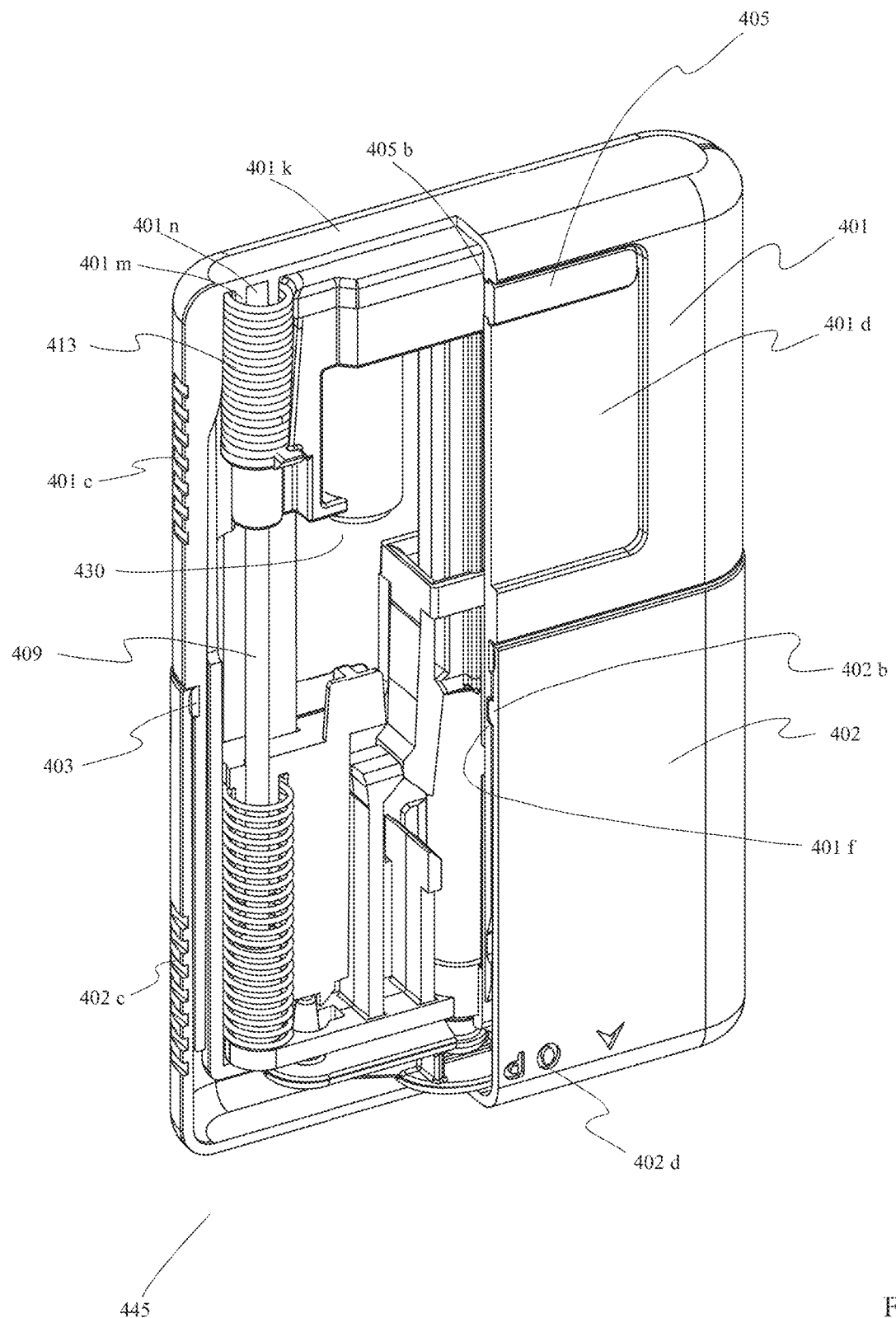
FIG. 18 shows the assembled medication delivery device of FIG. 12 with the internal assembly of FIG. 17.

FIG. 18 shows the internal assembly 445 within the housing 401 and the cover 402 of the medication delivery device 400 with a partial section through the housing 401, cover 402, seal 403, large window 405, actuator 406 and chassis 408. The seal 403 is made from a compliant material such as closed cell polyurethane foam that provides a waterproof seal between the housing 401 and the cover 402, and will allow the cover 402 to be removed and replaced without being damaged. One or more cover protrusions 402b extend outwards from the distal end of the inner surface of the cover 402 and engage with the upper cover indent 401f (or optionally lower cover indent 401g). This engagement provides means of locking the cap 402 to the housing 401 in one or more preferred positions. Indicia 402d may be provided in or on the cover 402. Cover grips 402c may be provided on the outer surface of the cover 402 to aid gripping by fingers. Housing grips 401c may be provided on the outer surface of the housing 401 to aid gripping by fingers. A labelling recess 401d may be provided on the outer surface of housing 401. The large window 405 and the small windows 404 are transparent and may be attached to the respective large window aperture 405b and small window aperture 404b using glue, solvent, ultrasonic welding, mechanical clips or any other industry method of attachment. The large window 405 can be used for inspecting the medicament 433 while the small windows 404 can be used to inspect the correct functioning of medication delivery device 400. The compressed vial spring 413 is shown between the vial spring platform 411j and the housing spring guide 401m attached to housing end plate 401k. A housing spring guide bearing 401n allows the guide rail 409 to slide inside it freely. The overall dimensions of the medication delivery device 400 in this configuration are substantially 84.5×53.5×13.7 mm although it can of course be made larger or smaller. For example, the device could have dimensions falling anywhere between 100×70×20 mm and 70×40×5 mm.

Figure 19:
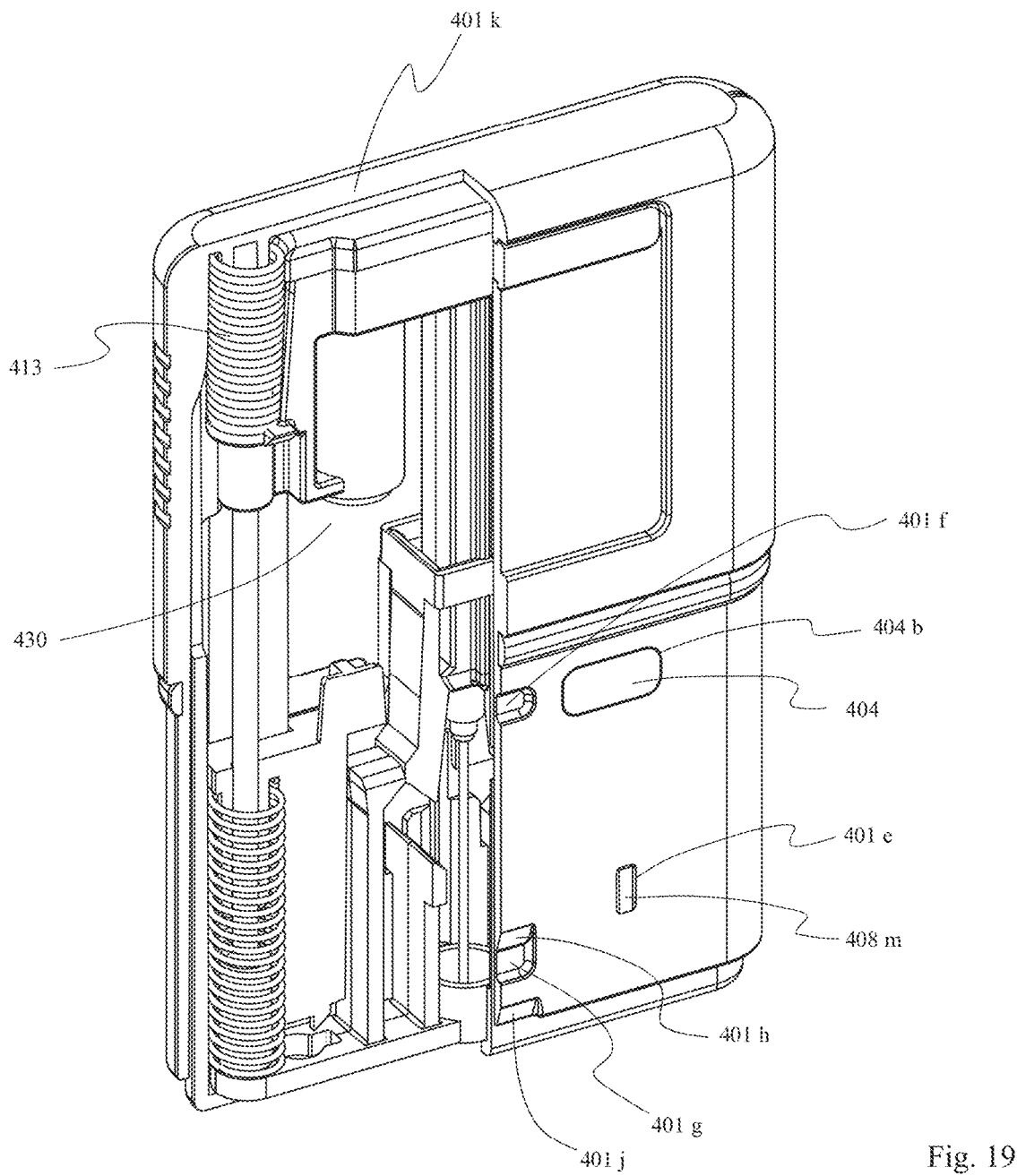
FIG. 19 shows the assembled medication delivery device with some components removed.

FIG. 19 shows the assembled medication delivery device 400 with the cover 402, safety plug 417 and needle cover subassembly 434, removed to reveal a small window 404 in small window aperture 404b. The compressed vial spring 413 exerts a force to try and push the vial subassembly 430 away from housing end plate 401k. The vial subassembly 430 is not able to move as the vial catch 432 cannot pass through the chassis lock 414, as previously detailed. The housing 401 is locked to the chassis 408 via the chassis assembly protrusion 408m located in the housing assembly hole 401e thereby locking the chassis 408 to the housing 401. The housing 401 is made of a pliable material such as ABS or acetal that can be deformed enough for the internal assembly 445 to be passed inside.

Figure 20:
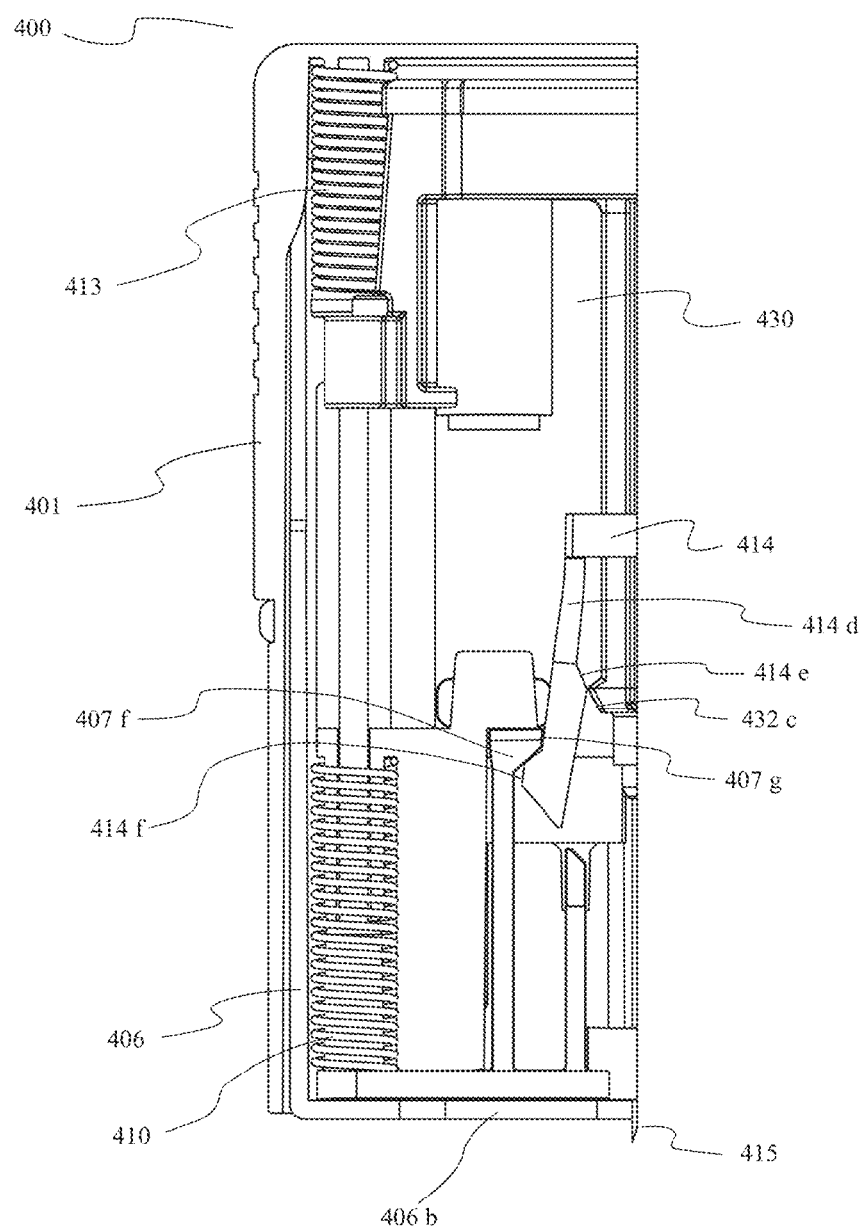
FIG. 20 shows a front elevation of one half of the assembled medication delivery device of FIG. 19 in a firing position.

FIG. 20 shows a front elevation of one half of the medication delivery device 400 so that relative movements between components are easier to discern. The actuator 406 is now shown in a firing position in which it has been pushed, via force applied to the actuator base plate 406b, into the housing 401. This further compresses the actuator spring 410, until the arm lock inner stop face 407g has moved past the chassis lock 414 outer stop face 414f. The vial spring 413 is now free to expand and push the vial subassembly 430 (with needle cover subassembly 440 removed) through the chassis lock 414. As the chassis tabs 414d are no longer constrained from moving by the arm lock 407f the vial catch lower face 432c can therefore slide past inner stop face 414e. The vial subassembly 430 is shown at the moment it has descended to the point at which the vial catch 432 has pushed apart chassis tabs 414d by the maximum amount. This is the start of the penetration stage and the sharpened proximal end of the hypodermic needle 415 has moved beyond the actuator base late 406b.

Figure 21:
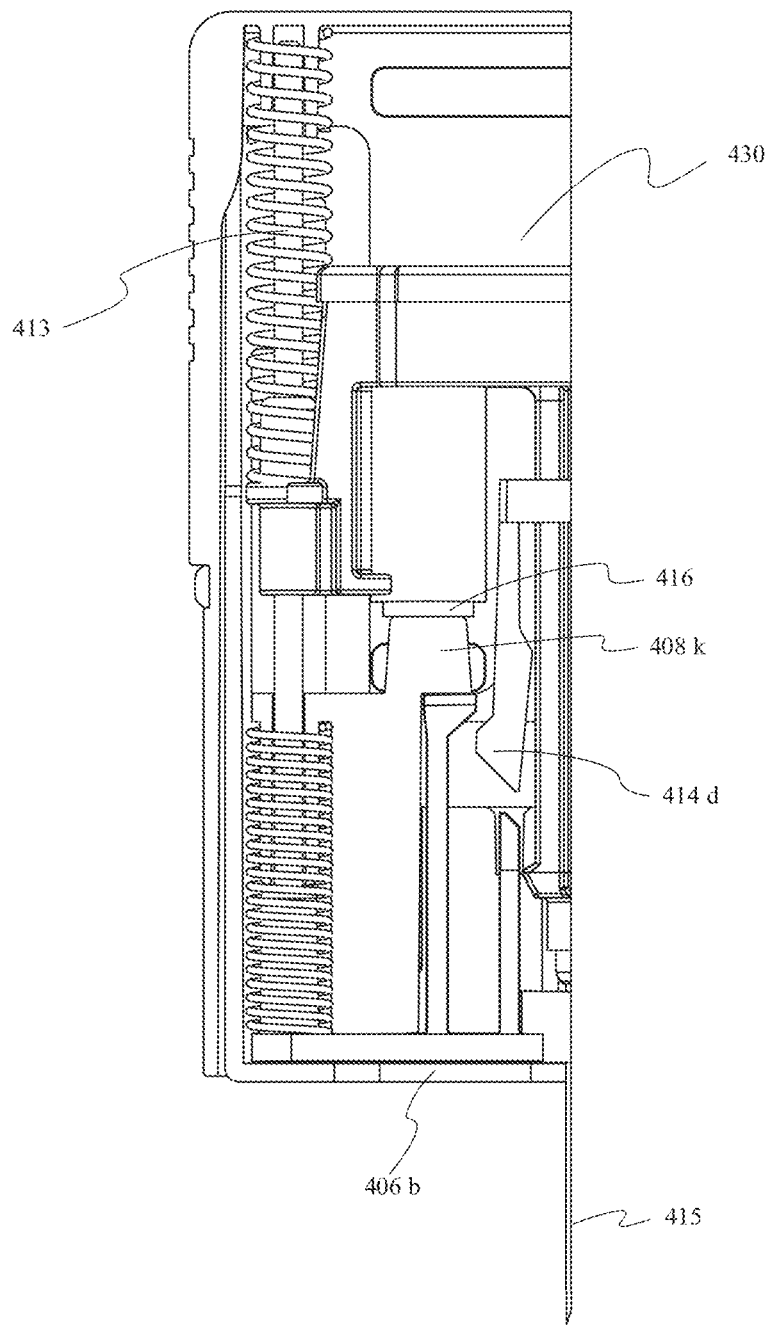
FIG. 21 shows a front elevation of the device of FIG. 19 in a penetration stage.

FIG. 21 shows the moment at which the vial subassembly 430 (with needle cover subassembly 440 removed) has been pushed by the expanding vial spring 413 until the plungers 416 have made contact with the plunger pushers 408k and the proximal end of the hypodermic needle 415 is now substantially beyond the actuator base plate 406b. The moment wherein plungers 416 have made contact with the plunger pushers 408k signifies the end of the penetration stage. The remaining force exerted by the expanding vial spring 413 is sufficient to continue to push the vial subassembly 430 towards the chassis 414 so that the plunger pushers 408k force the plungers 416 into the bores 411a and force the medicament 433 to flow through the hypodermic needle 415. The plunger pushers 408k therefore provide an analogous function to the stop wall of the previous embodiments and can be considered to be stop walls themselves. The chassis tab 414d can be seen having sprung back to the position before it was in before being stretched open by the vial catch 432. This is the beginning of the injection stage.

Figure 22:
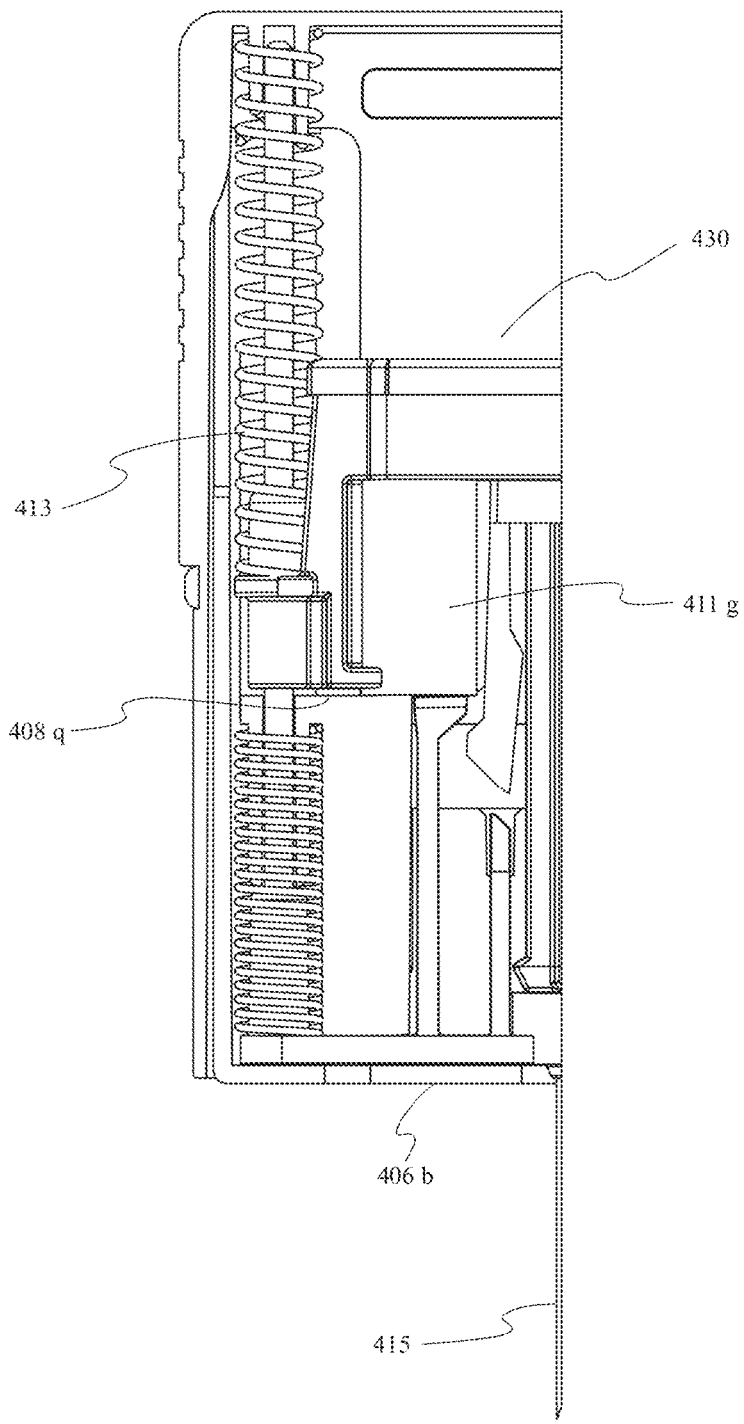
FIG. 22 shows a front view of one half of the device of FIG. 19 in an injection stage.

FIG. 22 shows the final resting position of the vial subassembly 430 (with the needle cover subassembly 440 removed) when it has been pushed by the expanding vial spring 413 until the plungers 416 have been fully pressed into the bores 411a by plunger pushers 408k, the proximal end of the hypodermic needle 415 is now at its full extent beyond the actuator base plate 406b and the proximal end of cylinder 411g is now contacting chassis central platform 408q. This is the end of the injection stage.

Figure 23:
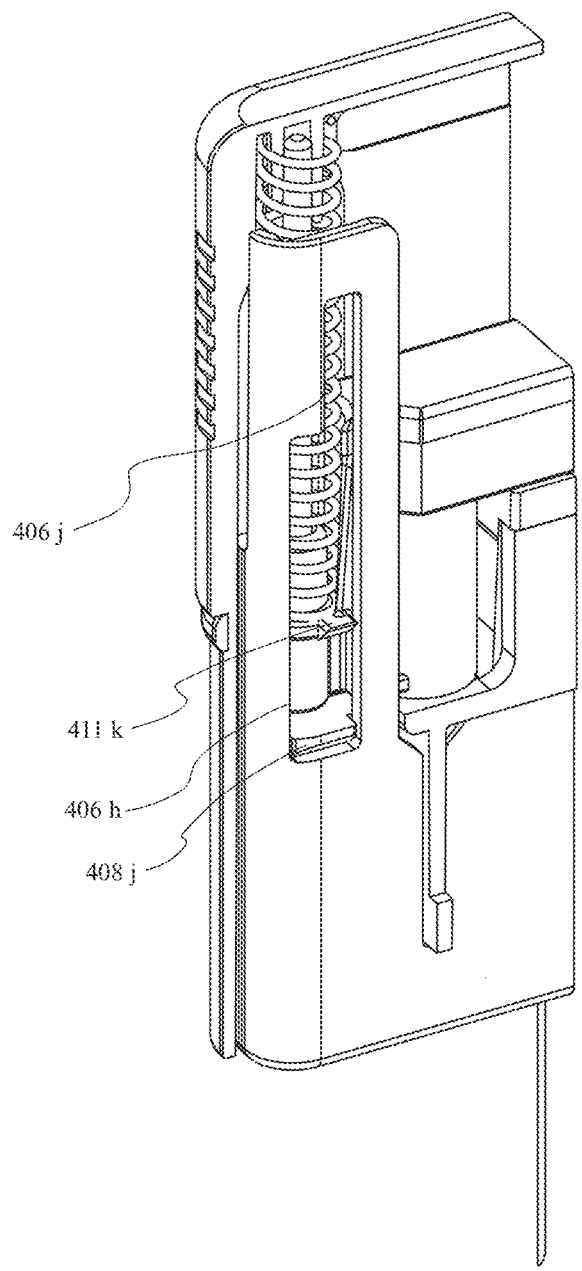
FIG. 23 shows a perspective view of one half of the device of FIG. 19 with a partial section through the housing and seal.

FIG. 23 shows the position of the chassis clip 408j and the vial clip 411k within the wide guide 406h and the narrow guide 406j in the final resting position of the vial subassembly 430.

Figure 24:
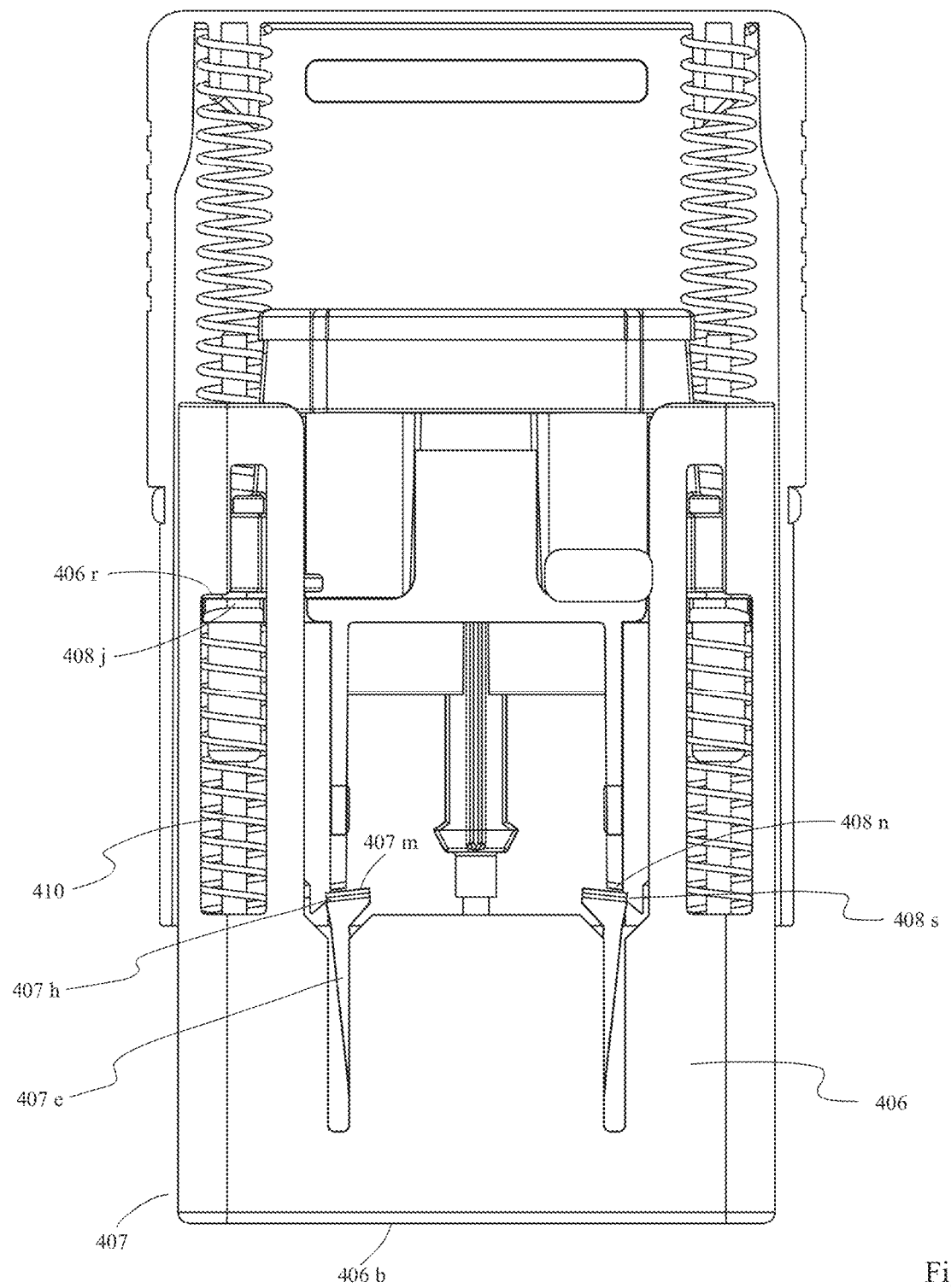
FIG. 24 shows a partial sectional front view of the device of FIG. 19.

FIG. 24 shows the position to which the actuator 406 moves when force is removed from the actuator base plate 406b. The actuator springs 410 expand and push the actuator 406, via the actuator lock 407, until the intermediate face 406r makes contact with the chassis clips 408j. With the actuator 406 in this position, the actuator lock arms 407e are able to spring open to their original positions as shown in FIG. 14 in which the arm lock outer stop face 407h now makes contact with the chassis extension stop face 408s and the chassis extension lock face 408n now sits above the arm lock outer top face 407m. Any force now applied to the actuator base plate 406b results in contact between the chassis extension lock face 408n and arm lock outer top face 407m preventing the actuator 406 from moving sufficiently to expose the proximal end of hypodermic needle 415. In this position the actuator 406 is locked relative to the housing 401 and the hypodermic needle 415, thereby preventing accidental injury due to contact with the hypodermic needle 415.

Figure 25:
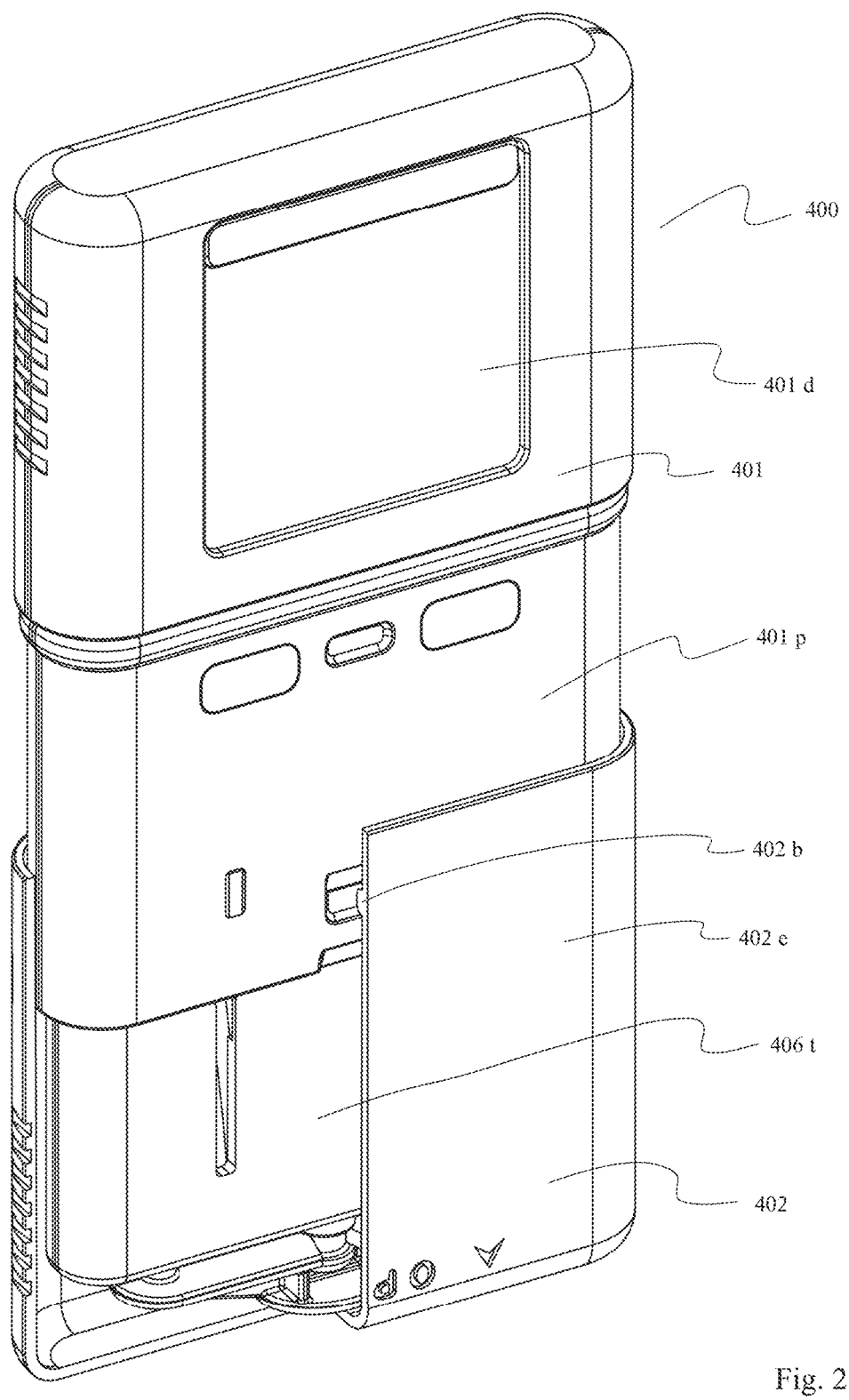
FIG. 25 shows a partial sectional perspective view of the device of FIG. 19.

FIG. 25 shows the medication delivery device 400 with the cap 402 fitted to the housing 401 in a second position with the cover protrusion 402b engaged in the lower cover indent 401g. The combined safety cover 417/needle cover subassembly 434 are shown having been (optionally) refitted to the seal surface 411e of the vial 411. Printing or labelling may be applied to labelling recess 401d, lower labelling face 401p, cover labelling face 402e and/or actuator labelling face 406t. FIG. 25 shows the final configuration of the medication delivery device 400 after it has been triggered by removing the combined safety cover 417/needle cover subassembly 434. Sufficient force is applied to the actuator lock platform 407b to further compress the actuator spring 410 and move the arm lock 407f away from the chassis lock 414 outer stop face 414f. This allows the chassis tabs 414d to spring apart and the vial catch 432 to slip through the chassis lock 414. This results in the plungers 416 striking the plunger pushers 408k, moving the plungers 416 into the bores 411a to force the medicament 433 through the hypodermic needle 415. After the actuation and injection removal of the force to the actuator lock platform 407b allows the actuator 406 to be pushed to a position in which it covers the hypodermic needle 415. The actuator 406 is locked into this position by interaction between the arm lock outer top face 407m and the chassis extension lock face 408n.

Functionally, therefore, the examples shown in FIGS. 12 to 24 operate in the same manner as the examples of FIGS. 1 to 11c. The vial springs 413 perform the same function as the energy storage springs 103 in propelling the needle in order to position the needle in the patient's tissue and then to administer the medicament. The actuator springs 330, 410 of both examples are used to provide a safety mechanism that shields the needle once an injection has been performed.

Figure 26:
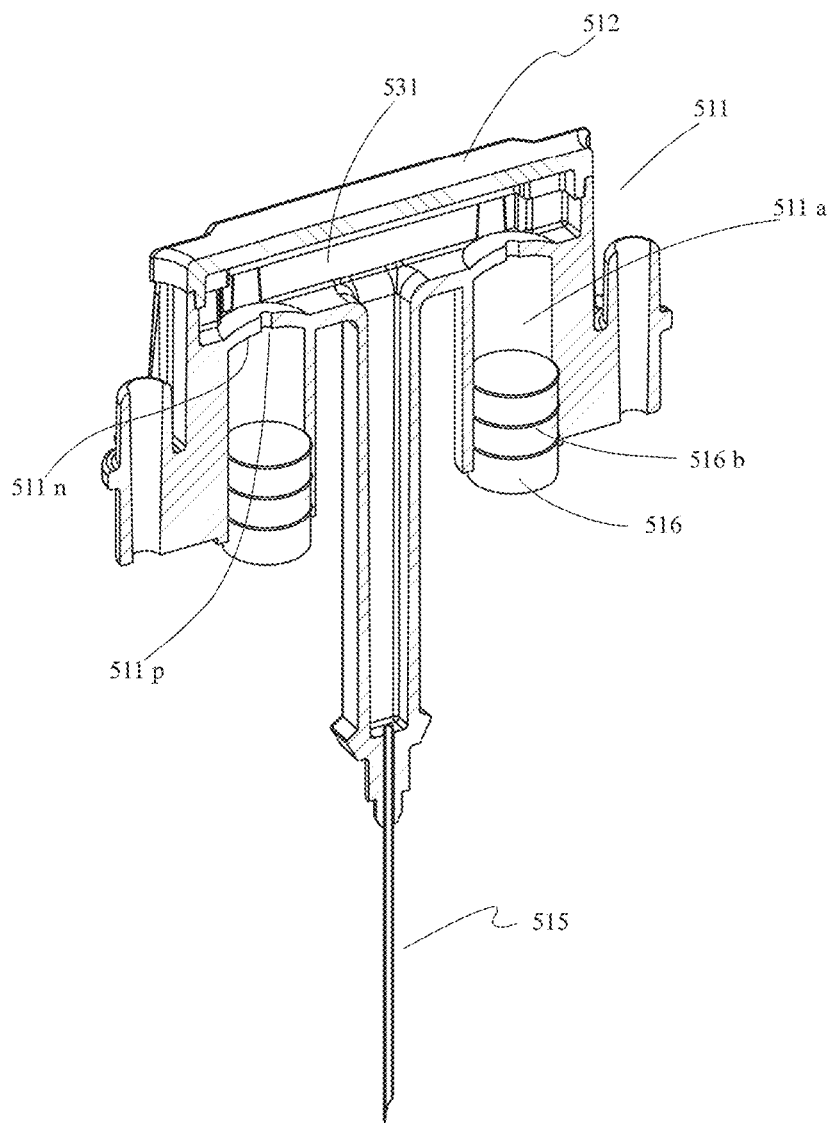
FIG. 26 shows a half section perspective view of a further embodiment of a vial subassembly of a medication delivery device.

FIG. 26 shows a further embodiment of a vial 511 for use in the delivery device of FIG. 12. The vial 511 is generally of similar construction to the above embodiments of a vial. As with the previous embodiments the vial comprises a pair of bores 511a. Each bore 511a has a pressure wall 511n located at its distal end. The pressure wall 511n is shown with a domed profile extending into a top cavity 531 of the vial 511. In some embodiments the domed profile could be provided to extend in the opposite direction or remain flat. The pressure wall 511n could also be positioned further inside the bore 511a, in other words, positioned less distally. Each pressure wall 511n has one or more pressure relief holes 511p through it. The holes in this example are of circular cross section but may instead be of any cross section. A typical cross-sectional area of the pressure relief hole 511p would be equivalent to a single hole of substantially 0.5 mm diameter. The hole is preferably of between 0.2 mm and 1 mm diameter. A plurality of pressure relief holes may be used instead of a single pressure relief hole.

When the plunger 516 moves from the proximal end of bore 511a towards the distal end, the pressure wall 511n and pressure relief holes 511p allow pressure in the medicament 533 to be at a much higher level in the bore 511a before it flows through the pressure relief holes 511p to a lower pressure level in the vial top cavity 531 and onwards to the hypodermic needle 515. In this way, pressure levels in the top cavity 531 do not rise to a level in which the medicament 533 pressure could rupture the vial cover 512 from the vial 511.

Whilst use of the various syringes described above have been described mainly in the context of an injection device, it will be appreciated that other applications e.g. for manually administering medication as a prefilled syringe in a patient or an IV tube, are also envisaged.

From reading the present disclosure, other variations and modifications will be apparent to the skilled person. It will be appreciated that various alterations could be made to the above described examples. The various examples and embodiments described herein can be combined in any combination. All of the features and components are optional for inclusion and combinable unless expressly indicated otherwise. Variations and modifications may involve equivalent and other features which are already known in the art, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The applicant hereby gives notice that new claims may be formulated to such features and/or combinations of such features during the prosecution of the present application or of any further application derived therefrom. Features of the devices and systems described may be incorporated into/used in corresponding methods.

For the sake of completeness, it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

The invention claimed is:

1. A syringe for use in a medication delivery device, the syringe comprising:
   a plunger; and
   a vial configured to contain medication, the vial comprising
      a chamber, and
      a needle attachment point, for attachment of a hypodermic needle, wherein the chamber is laterally offset from the needle attachment point such that the needle attachment point does not align with any part of the chamber;
   wherein the chamber is configured to receive the plunger so as to expel the medication from the vial; and
   wherein, during medication delivery, the medication is delivered to a patient in a medication delivery direction, and the plunger moves into the chamber to provide a plunging action in a direction counter to the medication delivery direction.

2. The syringe according to claim 1 wherein the chamber is a pair of chambers, the plunger is a pair of plungers, and each chamber is configured to receive one of the plungers.

3. The syringe according to claim 2 wherein the pair of chambers are arranged symmetrically about the needle attachment point.

4. The syringe according to claim 1 wherein the chamber has a substantially cylindrical or rectangular cross section at least in part, and/or wherein the chamber comprises a plurality of connected chambers, and wherein a pressure relief hole is provided between at least two of the connected chambers.

5. The syringe according to claim 1 comprising an attachment means, wherein the attachment means is configured to receive and/or cooperate with a reciprocal attachment means of a syringe carrier.

6. The syringe according to claim 5 wherein the attachment means of the syringe is or comprises a female attachment means and, optionally, wherein the female attachment means is or comprises a slot, bearing or hole, and/or wherein the attachment means of the syringe is formed in a wall, surface or body of the vial.

7. A medication delivery device comprising:
   a housing, having a distal end and a proximal end;
   an energy storage means;
   an actuator assembly; and
   the syringe according to claim 1, attached to the energy storage means, wherein the actuator assembly is configured to actuate the energy storage means to move the syringe towards the proximal end.

8. The medication delivery device according to claim 7, wherein the energy storage means is provided within the distal end of the housing.

9. The medication delivery device according to claim 7, wherein the actuator assembly has a distal end and a proximal end and wherein the distal end of the actuator assembly is provided within the housing and the proximal end of the actuator assembly extends beyond the housing.

10. The medication delivery device according to claim 7 wherein the syringe is configured to be movable through a penetration stage and an injection stage.

11. The medication delivery device according to claim 10 wherein a tip of a needle is moved into an injection positioned in a patient's tissue during the penetration stage and wherein the medication is injected into the patient's tissue during the injection stage.

12. The medication delivery device according to claim 10 wherein the syringe is configured to be moved through a distance in the injection stage which is less than half of a distance the syringe is configured to be moved through in the penetration stage.

13. The medication delivery device according to claim 10 wherein the syringe is moved through the penetration stage and/or injection stage via application of a force derived from the energy storage means.

14. The medication delivery device according to claim 10, wherein the housing, a proximal actuator part or other component of the medication delivery device comprises a stop wall, and wherein the stop wall is configured to cooperate with the plunger to transition the syringe from the penetration stage to the injection stage.

15. The medication delivery device according to claim 7 further comprising a syringe carrier and wherein the syringe carrier optionally comprises an attachment means configured to receive and/or cooperate with a reciprocal attachments means of the vial, and/or wherein the attachment means of the syringe carrier is or comprises a male attachment means or a guide rail and, optionally, wherein the male attachment means or guide rail is slidably connected to the syringe.

16. The medication delivery device according to claim 7 wherein a proximal end of the actuator assembly comprises a passage for a needle.

17. The medication delivery device according to claim 7 wherein the actuator assembly is configured to be actuated via application of a force at a proximal end of the actuator assembly and, optionally, via a manually applied force.

18. The medication delivery device according to claim 7 wherein the actuator assembly is configured to extend to cover a hypodermic needle attached to the needle attachment point after an injection is performed.

19. The medication delivery device according to claim 18 wherein the actuator assembly comprises a distal actuator part and a proximal actuator part, wherein the medication delivery device is further configured to translate the proximal actuator part away from the distal actuator part to cover the hypodermic needle after the injection is performed, and optionally, wherein the distal actuator part and the proximal actuator part comprise one or more corresponding detents, wherein the one or more corresponding detents are configured to disengage upon actuation of the medication delivery device.

* * * * *